United States Patent
Mosrin et al.

(10) Patent No.: US 10,875,858 B2
(45) Date of Patent: Dec. 29, 2020

(54) PROCESS FOR PREPARING HALOGENATED PYRIDINE DERIVATIVES

(71) Applicant: Bayer CropScience Aktiengesellschaft, Monheim am Rhein (DE)

(72) Inventors: Marc Mosrin, Cologne (DE); Ruediger Fischer, Pulheim (DE); Dominik Hager, Monheim (DE); Laura Hoffmeister, Duesseldorf (DE); Nina Kausch-Busies, Bergisch Gladbach (DE); David Wilcke, Duesseldorf (DE); Matthieu Willot, Duesseldorf (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/325,666

(22) PCT Filed: Aug. 9, 2017

(86) PCT No.: PCT/EP2017/070184
§ 371 (c)(1),
(2) Date: Feb. 14, 2019

(87) PCT Pub. No.: WO2018/033448
PCT Pub. Date: Feb. 22, 2018

(65) Prior Publication Data
US 2019/0202829 A1    Jul. 4, 2019

(30) Foreign Application Priority Data

Aug. 16, 2016  (EP) .................................. 16184368

(51) Int. Cl.
| C07D 471/04 | (2006.01) |
| C07D 491/056 | (2006.01) |
| C07D 487/04 | (2006.01) |
| B01J 31/24 | (2006.01) |

(52) U.S. Cl.
CPC ........ *C07D 471/04* (2013.01); *B01J 31/2404* (2013.01); *C07D 487/04* (2013.01); *C07D 491/056* (2013.01); *B01J 2531/824* (2013.01)

(58) Field of Classification Search
None
See application file for complete search history.

(56) References Cited

U.S. PATENT DOCUMENTS

| 8,030,305 | B2 * | 10/2011 | Lu .......................... A61P 19/02 514/248 |
| 2003/0069257 | A1 | 4/2003 | Li et al. |
| 2018/0016273 | A1 | 1/2018 | Fischer et al. |

FOREIGN PATENT DOCUMENTS

| WO | 2006065703 A1 | 6/2006 |
| WO | 2007075567 A1 | 7/2007 |
| WO | 2011027249 A2 | 3/2011 |
| WO | 2012086848 A1 | 6/2012 |
| WO | 2016124557 A1 | 8/2016 |

OTHER PUBLICATIONS

International Search Report issued in counterpart Application No. PCT/EP2017/070184, dated Oct. 30, 2017.
Wilson et al., "Copper- and Palladium-Catalyzed Amidation Reactions for the Synthesis of Substituted Imidazo[4,5-c]pyridines," The Journal of Organic Chemistry, (2014), vol. 79, No. 5: 2203-2212.
Barlin, "Ionisation Constants of Heterocyclic Substances. Part VIII. 1,3,5-Triazaindenes," Journal of the Chemical Society B: Physical Organic, (1966), vol. 0: 285-291.
Herz, et al., "2-Arylvinylation of 1-Methylindole by Palladium-Catalyzed Cross-Coupling Reactions," Synthesis, (1999), No. 6: 1013-1016.
Hammann, et al., "Cobalt-Catalyzed Negishi Cross-Coupling Reactions of (Hetero)Arylzinc Reagents with Primary and Secondary Alkyl Bromides and Iodides," Angew. Chem. Int. Ed., (2015), vol. 54, No. 15: 4478-4481.
Yokoyama, et al., "Stereoselective coupling of riboses with metallic salts of aromatic heterocycles," Journal of the Chemical Society, Perkin Transactions 1: Organic and Bio-Organic Chemistry, (1997), vol. 1:29-33.

* cited by examiner

*Primary Examiner* — Kamal A Saeed
(74) *Attorney, Agent, or Firm* — McBee Moore & Vanik IP, LLC

(57) ABSTRACT

The present invention relates to a process for preparing halogenated pyridine derivatives of the formula (II) proceeding from compounds of the structure Q-H via intermediates of the formula (IIIa) or (IIIb)

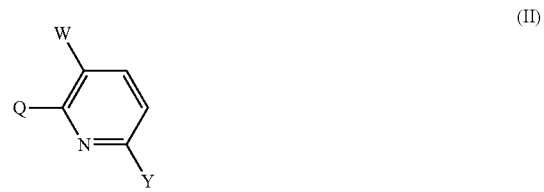

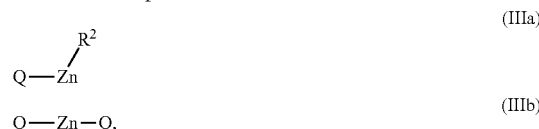

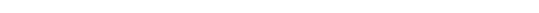

in which
Q is a structural element

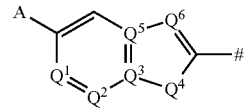

where the symbol # indicates the bond to the rest of the molecule and A, $Q^1$, $Q^2$, $Q^3$, $Q^4$, $Q^5$ and $Q^6$ have the definitions given in the description,
W is halogen,
Y is halogen, $CO_2R^1$ or $NO_2$, where $R^1$ is $(C_1-C_6)$-alkyl or $(C_1-C_6)$-haloalkyl, and
$R^2$ is halogen or —O-pivaloyl.

19 Claims, No Drawings

_US 10,875,858 B2_

PROCESS FOR PREPARING HALOGENATED PYRIDINE DERIVATIVES

CROSS-REFERENCE TO RELATED APPLICATIONS

This application is a National Stage entry of International Application No. PCT/EP2017/070184, filed Aug. 9, 2017, which claims priority to European Patent Application No. 16184368.5, filed Aug. 16, 2016.

BACKGROUND

Field

The present invention relates to a process for preparing halogenated pyridine derivatives of the formula (II)

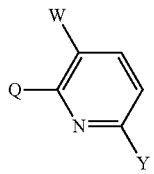

(II)

proceeding from compounds Q-H via intermediates of the formula (IIIa) or (IIIb)

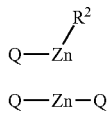

(IIIa)

(IIIb)

in which the structural elements shown in the formulae (II), (IIIa) and (IIIb) have the definitions given below. The invention further relates to halogenated pyridine derivatives and intermediates of this kind.

Description of Related Art

Halogenated pyridines derivatives of the formula (II) are of great industrial significance for the pharmaceutical and agrochemical industry and are an important intermediate, inter alia, in the preparation of compounds that are effective as pesticides, for example.

The literature discloses that compounds of the formula (II) can be prepared, for example, in a first step by condensation of pyridine-2-carboxylic acid derivatives with ortho-substituted bis(amine), amine alcohol or amine thiol (hetero)aryl derivatives in the presence of a condensing agent (cf. US2003/69257 or WO2006/65703) and then, in a second step, by further condensation as described in WO2012/86848. However, the chemical synthesis methods that have been described in the prior art to date for such halogenated pyridine derivatives very frequently make use of methods that are not economically implementable from an industrial point of view and/or have other disadvantages.

Disadvantages are low chemical yields, performance at very high temperatures (about 150 to 250° C.) and the possibility of difficult regio- and chemoselectivity of the condensation, especially in the case of imidazopyridine and imidazopyridazine derivatives. The preparation is therefore very expensive and unsuitable for industrial scale commercial processes. Moreover, corresponding compounds are barely commercially available. This is especially true of 3,6-dihalopyridine-2-carboxylic acid derivatives.

With regard to the disadvantages outlined above, there is an urgent need for a simplified, industrially and economically performable process for preparing halogenated pyridine derivatives, especially halogenated pyridine derivatives of the formula (II). The halogenated pyridine derivatives obtainable by this process sought are preferably to be obtained with good yield, high purity and in an economic manner.

SUMMARY

It has been found that, surprisingly, halogenated pyridine derivatives of the formula (II) can be prepared advantageously in a process using an organozinc base.

The present invention accordingly provides a process for preparing compounds of formula (II)

(II)

in which (configuration 1)
Q is a structural element

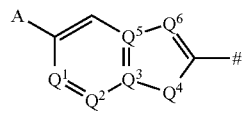

where the symbol # indicates the bond to the rest of the molecule and
$Q^1$ is N or $CR^6$,
$Q^2$ is N or $CR^6$,
$Q^3$ is N or C,
$Q^4$ is O, S, N or $NR^7$,
$Q^5$ is N or C,
$Q^6$ is N or CH,
$R^6$ is hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl,
$R^7$ is $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$ cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylthio-($C_1$-$C_4$)alkyl, ($C_1$-$C_4$)alkylsulphinyl-($C_1$-$C_4$)alkyl, ($C_1$-$C_4$)alkylsulphonyl-($C_1$-$C_4$)alkyl or ($C_1$-$C_4$)alkylcarbonyl-($C_1$-$C_4$)alkyl, and A is hydrogen, cyano, halogen, ($C_1$-$C_4$)alkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)alkoxyimino, ($C_1$-$C_4$)alkylthio, ($C_1$-$C_4$)haloalkylthio, ($C_1$-$C_4$)alkylsulphinyl, ($C_1$-$C_4$)haloalkylsulphinyl, ($C_1$-$C_4$)alkylsulphonyl, ($C_1$-$C_4$)haloalkylsulphonyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl or di-($C_1$-$C_4$)alkylaminosulphonyl, or A is —O—$CF_2$—O— and, together with $Q^1$ and the carbon atom to which it is bonded, forms a five-membered ring where $Q^1$ is carbon, W is halogen, and Y is halogen, $CO_2R^1$ or $NO_2$, where $R^1$ is ($C_1$-$C_6$)-alkyl or ($C_1$-$C_6$)-haloalkyl, characterized in that, in a first process step a), a compound Q-H in which Q is as defined above
is reacted with an organozinc base of the structure ($NR^3R^4$)—Zn—$R^2$ or ($NR^3R^4$)$_2$—Zn in which
$R^2$ is halogen or —O-pivaloyl and
$R^3$ and $R^4$ together form a —($CH_2$)$_4$—, —($CH_2$)$_5$— or —($CH_2$)$_2$O($CH_2$)$_2$— group, where each of these groups may optionally be substituted by 1, 2, 3 or 4 $R^5$ radicals and $R^5$ is selected from the group consisting of methyl, ethyl, n-propyl and i-propyl,
to give a compound of the formula (IIIa) or the formula (IIIb)

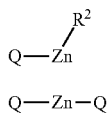
(IIIa)

Q—Zn—Q (IIIb)

in which Q and $R^2$ each have the definitions given above, and this compound of the formula (IIIa) or (IIIb) is reacted in a second process step b) with a compound of the formula (I)

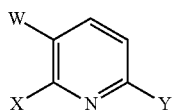
(I)

in which X is halogen and W and Y each have the definitions given above, in the presence of a catalyst, to give the compound of the formula (II).

DETAILED DESCRIPTION OF A PREFERRED EMBODIMENT

Preferably, $Q^1$, $Q^2$, $Q^3$, $Q^4$, $Q^5$ and $Q^6$ represent not more than five nitrogen atoms overall and further preferably not more than four nitrogen atoms overall.

Preferred and particularly preferred definitions of the Q, W, $R^1$, $R^2$, X and Y radicals included in the aforementioned formulae (I), (II), (IIIa) and (IIIb) of the process of the invention are elucidated hereinafter, with more specific description of the organozinc base further down, and so the preferred configurations of the base are specified at that point.

(Configuration 2)

Q is preferably a structural element from the group of Q1 to Q15

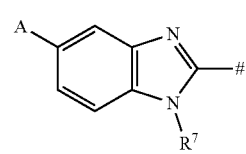
Q1

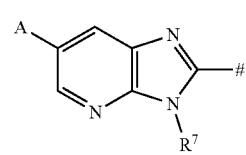
Q2

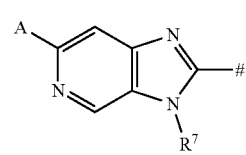
Q3

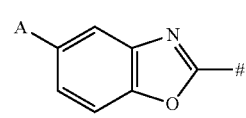
Q4

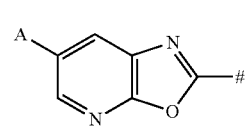
Q5

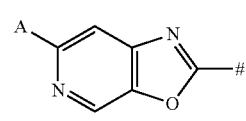
Q6

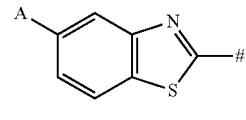
Q7

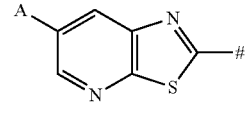
Q8

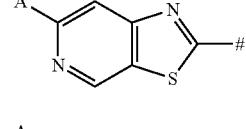
Q9

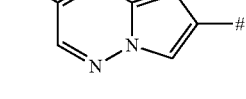
Q10

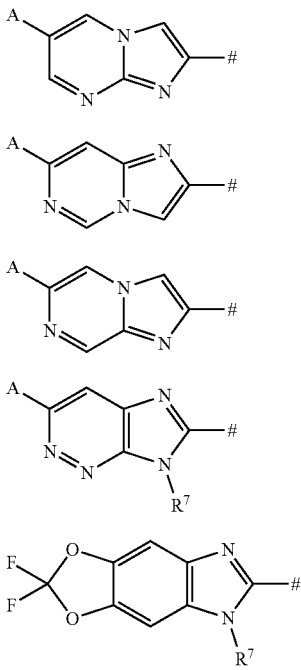

R[7] is preferably (C$_1$-C$_4$)alkyl, (C$_1$-C$_4$)haloalkyl, (C$_1$-C$_4$)alkoxy-(C$_1$-C$_4$)alkyl, (C$_1$-C$_4$)haloalkoxy-(C$_1$-C$_4$)alkyl, (C$_1$-C$_4$)alkylthio-(C$_1$-C$_4$)alkyl, (C$_1$-C$_4$)alkylsulphinyl-(C$_1$-C$_4$)alkyl, (C$_1$-C$_4$)alkylsulphonyl-(C$_1$-C$_4$)alkyl or (C$_1$-C$_4$)alkylcarbonyl-(C$_1$-C$_4$)alkyl, A is preferably fluorine, chlorine, bromine, fluoromethyl, difluoromethyl, trifluoromethyl, fluoroethyl (CH$_2$CFH$_2$, CHFCH$_3$), difluoroethyl (CF$_2$CH$_3$, CH$_2$CHF$_2$, CHFCFH$_2$), trifluoroethyl, (CH$_2$CF$_3$, CHFCHF$_2$, CF$_2$CFH$_2$), tetrafluoroethyl (CHFCF$_3$, CF$_2$CHF$_2$), pentafluoroethyl, trifluoromethoxy, difluorochloromethoxy, dichlorofluoromethoxy, trifluoromethylthio, trifluoromethylsulphinyl or trifluoromethylsulphonyl, W is preferably fluorine, chlorine or bromine, R[2] is preferably halogen, especially chlorine, bromine or iodine, X is preferably halogen, especially bromine or iodine, and Y is preferably fluorine, chlorine, bromine, CO$_2$R[1] or NO$_2$, where R[1] is (C$_1$-C$_4$)-alkyl.

(Configuration 3)

Q is more preferably a structural element from the group of Q2, Q3, Q10, Q12, Q14 and Q15

R[7] is more preferably (C$_1$-C$_4$)alkyl or (C$_1$-C$_4$)alkoxy-(C$_1$-C$_4$)alkyl, A is more preferably trifluoromethyl, fluoroethyl (CH$_2$CFH$_2$, CHFCH$_3$), difluoroethyl (CF$_2$CH$_3$, CH$_2$CHF$_2$, CHFCFH$_2$), trifluoroethyl, (CH$_2$CF$_3$, CHFCHF$_2$, CF$_2$CFH$_2$), tetrafluoroethyl (CHFCF$_3$, CF$_2$CHF$_2$), pentafluoroethyl, trifluoromethylthio, trifluoromethylsulphinyl or trifluoromethylsulphonyl, W is more preferably fluorine or chlorine, especially fluorine, R[2] is more preferably chlorine, X is more preferably bromine or iodine, especially iodine, and Y is more preferably chlorine, bromine, CO$_2$R[1] or NO$_2$, where R[1] is (C$_1$-C$_4$)-alkyl.

(Configuration 4)

Q is most preferably the structural element Q3 or Q14,

R[7] is most preferably methyl, ethyl, n-propyl or isopropyl, especially methyl, A is most preferably trifluoromethyl, W is most preferably fluorine, R[2] is most preferably chlorine, X is most preferably iodine, and Y is most preferably chlorine, bromine, CO$_2$R[1] or NO$_2$, where R[1] is methyl.

The radical definitions and elucidations given above apply both to the end products and intermediates and to the starting materials in a corresponding manner. These radical definitions can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

Very particular preference is given in accordance with the invention to those compounds in which there is a combination of the definitions listed above as being most preferred.

In a further preferred embodiment of the invention, Q is Q1 and R[7], A, W, R[2], X, and Y have the definitions given in configuration 1 or those given in configuration 2 or those given in configuration 3 or those given in configuration 4 (configuration 5).

In a further preferred embodiment of the invention, Q is Q2 and R[7], A, W, R[2], X, and Y have the definitions given in configuration 1 or those given in configuration 2 or those given in configuration 3 or those given in configuration 4 (configuration 6).

In a further preferred embodiment of the invention, Q is Q3 and R[7], A, W, R[2], X, and Y have the definitions given in configuration 1 or those given in configuration 2 or those given in configuration 3 or those given in configuration 4 (configuration 7).

In a further preferred embodiment of the invention, Q is Q4 and R[7], A, W, R[2], X, and Y have the definitions given in configuration 1 or those given in configuration 2 or those given in configuration 3 or those given in configuration 4 (configuration 8).

In a further preferred embodiment of the invention, Q is Q5 and R[7], A, W, R[2], X, and Y have the definitions given in configuration 1 or those given in configuration 2 or those given in configuration 3 or those given in configuration 4 (configuration 9).

In a further preferred embodiment of the invention, Q is Q6 and R[7], A, W, R[2], X, and Y have the definitions given in configuration 1 or those given in configuration 2 or those given in configuration 3 or those given in configuration 4 (configuration 10).

In a further preferred embodiment of the invention, Q is Q7 and R[7], A, W, R[2], X, and Y have the definitions given in configuration 1 or those given in configuration 2 or those given in configuration 3 or those given in configuration 4 (configuration 11).

In a further preferred embodiment of the invention, Q is Q8 and R[7], A, W, R[2], X, and Y have the definitions given in configuration 1 or those given in configuration 2 or those given in configuration 3 or those given in configuration 4 (configuration 12).

In a further preferred embodiment of the invention, Q is Q9 and R[7], A, W, R[2], X, and Y have the definitions given in configuration 1 or those given in configuration 2 or those given in configuration 3 or those given in configuration 4 (configuration 13).

In a further preferred embodiment of the invention, Q is Q10 and R$^7$, A, W, R$^2$, X, and Y have the definitions given in configuration 1 or those given in configuration 2 or those given in configuration 3 or those given in configuration 4 (configuration 14).

In a further preferred embodiment of the invention, Q is Q11 and R$^7$, A, W, R$^2$, X, and Y have the definitions given in configuration 1 or those given in configuration 2 or those given in configuration 3 or those given in configuration 4 (configuration 15).

In a further preferred embodiment of the invention, Q is Q12 and R$^7$, A, W, R$^2$, X, and Y have the definitions given in configuration 1 or those given in configuration 2 or those given in configuration 3 or those given in configuration 4 (configuration 16).

In a further preferred embodiment of the invention, Q is Q13 and R$^7$, A, W, R$^2$, X, and Y have the definitions given in configuration 1 or those given in configuration 2 or those given in configuration 3 or those given in configuration 4 (configuration 17).

In a further preferred embodiment of the invention, Q is Q14 and R$^7$, A, W, R$^2$, X, and Y have the definitions given in configuration 1 or those given in configuration 2 or those given in configuration 3 or those given in configuration 4 (configuration 18).

In a further preferred embodiment of the invention, Q is Q15 and R$^7$, A, W, R$^2$, X, and Y have the definitions given in configuration 1 or those given in configuration 2 or those given in configuration 3 or those given in configuration 4 (configuration 19).

Advantageously, the halogenated pyridine derivatives of the formula (II) can be prepared by the process according to the invention with good yields and in high purity. A great advantage of the process according to the invention is the regioselectivity thereof. Because of the very good functional group tolerance of zinc reagents, zinc bases are very attractive. Especially advantageous is the possibility of being able to conduct Negishi couplings even at distinctly lower temperatures, in which case even functional groups that are sensitive at higher temperatures, such as esters or fluorine atoms, are tolerated in processes according to the invention without impairing the regioselectivity that exists. Moreover, Negishi cross-couplings within the context of a process according to the invention can also give rise to good yields of target product in the presence of ortho substituents on the pyridine skeleton, even though such couplings with 2-substituted pyridine derivatives have to date been known for giving low yields. Thus, further and/or more flexible derivatizations of reactant and product are possible without having to constantly alter or adapt synthesis routes.

The process according to the invention can be elucidated by the following scheme (I):

Scheme (I)

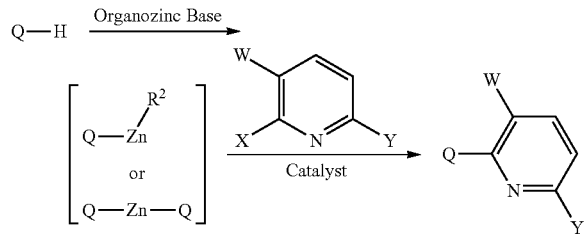

In this scheme, Q, W, R$^2$, X, and Y and, within the respective definitions, any further structural elements present each have the definitions given above. The compounds shown in brackets are the intermediate (formula IIIa or formula IIIb) which are reacted further with a compound of the formula (I) to give the compound of the formula (II). Accordingly, the process according to the invention can be divided into the two process steps a) and b), step a) being the conversion of the compound Q-H to the respective intermediate and step b) being the further conversion of the intermediate to the compound of the formula (II).

General Definitions

In the context of the present invention, the term halogen (Hal), unless defined otherwise, encompasses those elements selected from the group consisting of fluorine, chlorine, bromine and iodine.

The term "halides" in connection with the present invention describes compounds between halogens and elements of other groups of the Periodic Table, which can give rise to halide salts (ionic compounds (salts) which consist of anions and cations because of the great difference in electronegativity between the elements involved and are held together by electrostatic interactions) or covalent halides (covalent compounds where the difference in electronegativity is not as great as in the aforementioned ionic compounds, but the bonds have charge polarity), depending on the nature of the chemical bond. Particular preference is given in accordance with the invention to halide salts.

The term "pivaloyl" in the context of the present invention describes the deprotonated radical of pivalic acid (X) having the empirical formula $(CH_3)_3CCO_2H$.

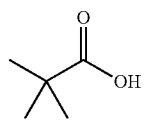

(X)

"O-pivaloyl" correspondingly means that the bond of the pivaloyl radical is via the deprotonated oxygen atom of the acid group.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, particular preference is given to $C_1$-$C_6$-alkyl radicals. Special preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood in the present case to mean an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms may be identical or different. Unless defined differently, halogen here is fluorine, chlorine, bromine or iodine, especially fluorine, chlorine or bromine. Alkyl groups substituted by one or more halogen atoms are (-Hal), for example, selected from trifluoromethyl ($CF_3$), difluoromethyl ($CHF_2$), $CF_3CH_2$, $ClCH_2$ or $CF_3CCl_2$.

Unless stated otherwise, optionally substituted radicals may be mono- or polysubstituted, where the substituents in the case of polysubstitutions may be the same or different.

The synthesis of compounds Q-H as reactants of a process according to the invention is known in principle to those skilled in the art. For example, compounds Q-H with Q=Q1, Q2, Q3, Q14 or Q15 can be obtained from corresponding pyridinediamine derivatives by ring closure to give the respective azole compound, as described, for example, in WO2014/100065 or WO2015/017610 preferably under acidic conditions. Alternative syntheses are likewise possible, but are more complex and as a result generally less economically advantageous.

The conversion of the compounds Q-H to compounds of the formula (IIIa) or (IIIb) in the first process step (step a)) is effected in the presence of an organozinc base of the structure $(NR^3R^4)$—Zn—$R^2$ or $(NR^3R^4)_2$—Zn, in which (configuration B-1)
$R^2$ is as defined above (configuration 1) (and is therefore halogen or —O-pivaloyl),
$R^3$ and $R^4$ together form a —$(CH_2)_4$—, —$(CH_2)_5$— or —$(CH_2)_2O(CH_2)_2$— group, where each of these groups may optionally be substituted by 1, 2, 3 or 4 $R^5$ radicals and
$R^5$ is selected from the group consisting of methyl, ethyl, n-propyl and i-propyl.

It is preferable that (configuration B-2)
$R^2$ is as defined above as preferred (configuration 2) (and is therefore halogen, especially chlorine, bromine or iodine),
$R^3$ and $R^4$ together form a —$(CH_2)_5$— group, where each of these groups may optionally be substituted by 1, 2, 3 or 4 $R^5$ radicals and
$R^5$ is selected from the group consisting of methyl and ethyl.

It is particularly preferable that (configuration B-3)
$R^2$ is as defined above as more preferred (configuration 3) or as most preferred (configuration 4) (and is therefore chlorine) and
$R^3$ and $R^4$ together form a —$(CH_2)_5$— group substituted by 4 methyl groups.

The radical definitions given above can be combined with one another as desired, i.e. including combinations between the respective ranges of preference.

In a very particularly preferred configuration of the base according to the invention, the structural element ($NR^3R^4$) is tetramethylpiperidine (TMP) of formula (IV).

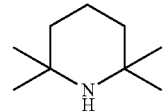

(IV)

Organozinc bases most preferred in accordance with the invention are accordingly characterized in that zinc is bound by TMP, especially in the form of zinc halide and most preferably in the form of zinc chloride. Bases of this kind have the following structure of the formula (V) (configuration B-4)

$$(TMP)_xZnCl_{2-x} \qquad (V)$$

in which x is the number 1 or 2. Among these, preference is given in turn to bases with x=1 (configuration B-5) of formula (VI):

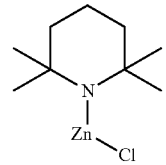

(VI)

In a further preferred embodiment of the process according to the invention, the organozinc base is present in conjunction with alkali metal or alkaline earth metal halides. This is especially true of bases of the formulae (V) and (VI). Particularly preferred alkali metal or alkaline earth metal halides of this kind are lithium chloride and magnesium chloride, very particular preference being given to lithium chloride. Organozinc bases that are very particularly preferred in accordance with the invention are accordingly TMP ZnCl.LiCl or $(TMP)_2$ Zn.2LiCl (configuration B-6). Most preferred is TMP ZnCl.LiCl (VII; configuration B-7).

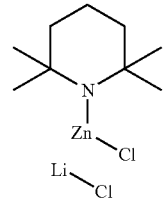

(VII)

Specific combinations of compounds of the formulae (I), (II) and (IIIa) or (IIIb) with bases according to the invention are cited hereinafter by way of example in Table 1, these being employable in a process according to the invention. Since, in some configurations, the structural element $R^2$ is present both in the base according to the invention and in the compound of the formula (IIIa), the narrowest definition applies to $R^2$ in each case.

TABLE 1

| Number | Compounds of the formulae (I), (II) and (IIIa) or (IIIb) | Base according to |
|---|---|---|
| 1 | Configuration 1 | Configuration B-1 |
| 2 | Configuration 1 | Configuration B-2 |
| 3 | Configuration 1 | Configuration B-3 |
| 4 | Configuration 1 | Configuration B-4 |
| 5 | Configuration 1 | Configuration B-5 |
| 6 | Configuration 1 | Configuration B-6 |
| 7 | Configuration 1 | Configuration B-7 |
| 8 | Configuration 2 | Configuration B-1 |
| 9 | Configuration 2 | Configuration B-2 |
| 10 | Configuration 2 | Configuration B-3 |
| 11 | Configuration 2 | Configuration B-4 |
| 12 | Configuration 2 | Configuration B-5 |
| 13 | Configuration 2 | Configuration B-6 |
| 14 | Configuration 2 | Configuration B-7 |
| 15 | Configuration 3 | Configuration B-1 |
| 16 | Configuration 3 | Configuration B-2 |
| 17 | Configuration 3 | Configuration B-3 |
| 18 | Configuration 3 | Configuration B-4 |
| 19 | Configuration 3 | Configuration B-5 |
| 20 | Configuration 3 | Configuration B-6 |
| 21 | Configuration 3 | Configuration B-7 |
| 22 | Configuration 4 | Configuration B-1 |
| 23 | Configuration 4 | Configuration B-2 |
| 24 | Configuration 4 | Configuration B-3 |
| 25 | Configuration 4 | Configuration B-4 |
| 26 | Configuration 4 | Configuration B-5 |
| 27 | Configuration 4 | Configuration B-6 |
| 28 | Configuration 4 | Configuration B-7 |
| 29 | Configuration 5 | Configuration B-1 |
| 30 | Configuration 5 | Configuration B-2 |
| 31 | Configuration 5 | Configuration B-3 |
| 32 | Configuration 5 | Configuration B-4 |
| 33 | Configuration 5 | Configuration B-5 |
| 34 | Configuration 5 | Configuration B-6 |
| 35 | Configuration 5 | Configuration B-7 |
| 36 | Configuration 6 | Configuration B-1 |
| 37 | Configuration 6 | Configuration B-2 |
| 38 | Configuration 6 | Configuration B-3 |
| 39 | Configuration 6 | Configuration B-4 |
| 40 | Configuration 6 | Configuration B-5 |
| 41 | Configuration 6 | Configuration B-6 |
| 42 | Configuration 6 | Configuration B-7 |
| 43 | Configuration 7 | Configuration B-1 |
| 44 | Configuration 7 | Configuration B-2 |
| 45 | Configuration 7 | Configuration B-3 |
| 46 | Configuration 7 | Configuration B-4 |
| 47 | Configuration 7 | Configuration B-5 |
| 48 | Configuration 7 | Configuration B-6 |
| 49 | Configuration 7 | Configuration B-7 |
| 50 | Configuration 8 | Configuration B-1 |
| 51 | Configuration 8 | Configuration B-2 |
| 52 | Configuration 8 | Configuration B-3 |
| 53 | Configuration 8 | Configuration B-4 |
| 54 | Configuration 8 | Configuration B-5 |
| 55 | Configuration 8 | Configuration B-6 |
| 56 | Configuration 8 | Configuration B-7 |
| 57 | Configuration 9 | Configuration B-1 |
| 58 | Configuration 9 | Configuration B-2 |
| 59 | Configuration 9 | Configuration B-3 |
| 60 | Configuration 9 | Configuration B-4 |
| 61 | Configuration 9 | Configuration B-5 |
| 62 | Configuration 9 | Configuration B-6 |
| 63 | Configuration 9 | Configuration B-7 |
| 64 | Configuration 10 | Configuration B-1 |
| 65 | Configuration 10 | Configuration B-2 |
| 66 | Configuration 10 | Configuration B-3 |
| 67 | Configuration 10 | Configuration B-4 |
| 68 | Configuration 10 | Configuration B-5 |
| 69 | Configuration 10 | Configuration B-6 |
| 70 | Configuration 10 | Configuration B-7 |
| 71 | Configuration 11 | Configuration B-1 |
| 72 | Configuration 11 | Configuration B-2 |
| 73 | Configuration 11 | Configuration B-3 |
| 74 | Configuration 11 | Configuration B-4 |
| 75 | Configuration 11 | Configuration B-5 |
| 76 | Configuration 11 | Configuration B-6 |
| 77 | Configuration 11 | Configuration B-7 |
| 78 | Configuration 12 | Configuration B-1 |
| 79 | Configuration 12 | Configuration B-2 |
| 80 | Configuration 12 | Configuration B-3 |
| 81 | Configuration 12 | Configuration B-4 |
| 82 | Configuration 12 | Configuration B-5 |
| 83 | Configuration 12 | Configuration B-6 |
| 84 | Configuration 12 | Configuration B-7 |
| 85 | Configuration 13 | Configuration B-1 |
| 86 | Configuration 13 | Configuration B-2 |
| 87 | Configuration 13 | Configuration B-3 |
| 88 | Configuration 13 | Configuration B-4 |
| 89 | Configuration 13 | Configuration B-5 |
| 90 | Configuration 13 | Configuration B-6 |
| 91 | Configuration 13 | Configuration B-7 |
| 92 | Configuration 14 | Configuration B-1 |
| 93 | Configuration 14 | Configuration B-2 |
| 94 | Configuration 14 | Configuration B-3 |
| 95 | Configuration 14 | Configuration B-4 |
| 96 | Configuration 14 | Configuration B-5 |
| 97 | Configuration 14 | Configuration B-6 |
| 98 | Configuration 14 | Configuration B-7 |
| 99 | Configuration 15 | Configuration B-1 |
| 100 | Configuration 15 | Configuration B-2 |
| 101 | Configuration 15 | Configuration B-3 |
| 102 | Configuration 15 | Configuration B-4 |
| 103 | Configuration 15 | Configuration B-5 |
| 104 | Configuration 15 | Configuration B-6 |
| 105 | Configuration 15 | Configuration B-7 |
| 106 | Configuration 16 | Configuration B-1 |
| 107 | Configuration 16 | Configuration B-2 |
| 108 | Configuration 16 | Configuration B-3 |
| 109 | Configuration 16 | Configuration B-4 |
| 110 | Configuration 16 | Configuration B-5 |
| 111 | Configuration 16 | Configuration B-6 |
| 112 | Configuration 16 | Configuration B-7 |
| 113 | Configuration 17 | Configuration B-1 |
| 114 | Configuration 17 | Configuration B-2 |
| 115 | Configuration 17 | Configuration B-3 |
| 116 | Configuration 17 | Configuration B-4 |
| 117 | Configuration 17 | Configuration B-5 |
| 118 | Configuration 17 | Configuration B-6 |
| 119 | Configuration 17 | Configuration B-7 |
| 120 | Configuration 18 | Configuration B-1 |
| 121 | Configuration 18 | Configuration B-2 |
| 122 | Configuration 18 | Configuration B-3 |
| 123 | Configuration 18 | Configuration B-4 |
| 124 | Configuration 18 | Configuration B-5 |
| 125 | Configuration 18 | Configuration B-6 |
| 126 | Configuration 18 | Configuration B-7 |
| 127 | Configuration 19 | Configuration B-1 |
| 128 | Configuration 19 | Configuration B-2 |
| 129 | Configuration 19 | Configuration B-3 |
| 130 | Configuration 19 | Configuration B-4 |
| 131 | Configuration 19 | Configuration B-5 |
| 132 | Configuration 19 | Configuration B-6 |
| 133 | Configuration 19 | Configuration B-7 |

Preferably, the organozinc base is used in the process according to the invention in a total amount of 0.5 to 5 equivalents, preferably of 0.8 to 2 equivalents, further preferably of 1 to 1.5 equivalents and more preferably of 1.0 to 1.2 equivalents, based on the compound Q-H. One advantage of the process according to the invention in this regard is that the organometallic base can be used in virtually stoichiometric amounts.

Depending on whether the structural element (NR³R⁴) is present once or twice in the organozinc base used, intermediate compounds of the formula (IIIa) or of the formula (IIIb) are formed in process step a).

The conversion of the compounds of the formula (IIIa) or (IIIb) to compounds of the formula (II) in the second process step (step b)) is effected in the presence of a compound of the formula (I)

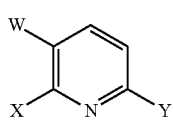

in which X, W and Y each have the definitions given above.

During the Negishi cross-coupling, the reaction takes place virtually exclusively at position 2, since iodine is the best leaving group on the pyridine skeleton. It then regioselectively affords the corresponding pyridine derivative of the formula (II).

Compounds of the formula (I) can be obtained, for example, by substitution of an appropriate precursor compound, i.e. a pyridine derivative with the W and Y radicals, by the X radical. Such a substitution can be effected, for example, by metallation of the precursor compound in the presence of zinc bases and subsequent reaction with elemental halogen. Metallations of this kind with substituted pyridines, for example, at the 4 position are described in Angewandte Chemie 2007 (46), p. 7685ff or Organic Letters 2009 (11), p. 1837ff.

Preferably, the compound of the formula (I) is used in the process according to the invention in a total amount of 0.5 to 10.0 equivalents, preferably of 0.8 to 5 equivalents, further preferably of 1 to 2.5 equivalents and more preferably of 1.0 to 1.5 equivalents or more preferably of 1.5 to 2.0 equivalents or more preferably of 1.0 to 2.0 equivalents, based on the compound Q-H.

The conversion in process step b) is further effected in the presence of a catalyst. Preferably, the catalyst is a palladium compound or a nickel compound. More preferably, the catalyst is a palladium compound. It is most preferably tetrakis(triphenylphosphine)palladium(0), abbreviated to Pd(PPh$_3$)$_4$, of the formula (IX).

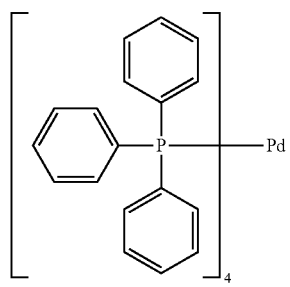

Typically, in a process according to the invention, 2.5-25 mol % and preferably 5-20 mol % of catalyst is used.

The inventive conversion of the compounds Q-H to compounds of the formula (IIIa) or (IIIb) and further to compounds of the formula (II) is preferably effected in the presence of an organic solvent in each case. Useful solvents in principle include all organic solvents which are inert under the reaction conditions employed and in which the compounds to be converted have adequate solubility. Suitable solvents especially include: tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); N,N'-dimethylpropyleneurea (DMPU), halohydrocarbons and aromatic hydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, especially 1,2-dichlorobenzene, chlorotoluene, trichlorobenzene; 4-methoxybenzene, fluorinated aliphatics and aromatics, such as trichlorotrifluoroethane, benzotrifluoride and 4-chlorobenzotrifluoride. It is also possible to use solvent mixtures, preferably mixtures of the aforementioned solvents such as tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, dimethylformamide (DMF).

Preferred solvents are THF, N,N-dimethylformamide (DMF), 1,4-dioxane, diglyme, methyl tert-butyl ether (MTBE), tert-amyl methyl ether (TAME), 2-methyl-THF, toluene and 4-methoxybenzene.

Particularly preferred solvents are THF and N,N-dimethylformamide (DMF), very particular preference being given to THF.

The solvent may also be degassed (oxygen-free).

Preference is given to using the same solvent for both process steps a) and b). Alternative configurations of the invention in which different solvents are used for process steps a) and b) are likewise possible, however, in which case the solvents are likewise preferably selected from the aforementioned solvents, and the respective solvents specified as being preferred, more preferred and most preferred are applicable to the respective process step a) or b).

The conversion in process step a) is generally conducted at a temperature between 0° C. and 80° C. and with increasing preference between 10° C. and 70° C., between 15° C. and 60° C., between 20° C. and 50° C., between 20° C. and 40° C., and most preferably between 20° C. and 35° C., for example at room temperature or 25° C.

The conversion in process step b) is generally conducted at a temperature between 40° C. and 90° C. and with increasing preference between 50° C. and 85° C., between 55° C. and 80° C., between 60° C. and 80° C., and most preferably between 65° C. and 75° C., for example at 65° C.

The reaction is typically conducted at standard pressure, but can also be conducted at elevated or reduced pressure.

The desired compounds of the formula (II) can be isolated, for example, by aqueous workup in the presence of saturated ammonium chloride or sodium thiosulphate solutions and/or subsequent chromatography. Such processes are known to those skilled in the art and also include crystallization from an organic solvent or solvent mixture.

One example of a particularly preferred embodiment of the process according to the invention can be elucidated with reference to the following scheme (II):

Scheme II:

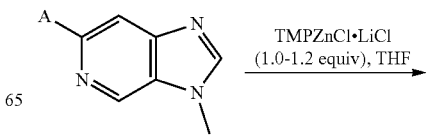

-continued $$[\text{A}\text{-imidazopyridine-ZnCl}] \xrightarrow[\text{Pd(0), THF}]{(1.0\text{-}1.2 \text{ equiv}),} \text{product}$$

In this scheme, A, W and Y have the definitions given above. The compound shown in brackets represents the corresponding intermediate of the formula IIIa which is converted further to the product, a compound of the formula (II). Both reactions take place in THF as solvent. "equiv" refers to the amount of equivalents of TMPZnCl.LiCl or compound of the formula (I) used. Pd(0) represents a palladium compound as catalyst, preferably in the form of $Pd(PPh_3)_4$.

The present invention further provides compounds of the structure Q-H in which (configuration Q-H-1-1)
Q is a structural element where the symbol # indicates the bond to the rest of the molecule and
$Q^1$ is N or $CR^6$,
$Q^2$ is N or $CR^6$,
$Q^3$ is N or C,
$Q^4$ is O, S, N or $NR^7$,
$Q^5$ is N or C,
$Q^6$ is N or CH,
$R^6$ is hydrogen, $(C_1\text{-}C_4)$alkyl, $(C_1\text{-}C_4)$haloalkyl, $(C_1\text{-}C_4)$cyanoalkyl, $(C_1\text{-}C_4)$hydroxyalkyl, $(C_1\text{-}C_4)$alkoxy-$(C_1\text{-}C_4)$alkyl, $(C_1\text{-}C_4)$haloalkoxy-$(C_1\text{-}C_4)$alkyl, $(C_2\text{-}C_4)$alkenyl, $(C_2\text{-}C_4)$alkenyloxy-$(C_1\text{-}C_4)$alkyl, $(C_2\text{-}C_4)$haloalkenyloxy-$(C_1\text{-}C_4)$alkyl, $(C_2\text{-}C_4)$haloalkenyl, $(C_2\text{-}C_4)$cyanoalkenyl, $(C_2\text{-}C_4)$alkynyl, $(C_2\text{-}C_4)$alkynyloxy-$(C_1\text{-}C_4)$alkyl, $(C_2\text{-}C_4)$haloalkynyl, $(C_3\text{-}C_6)$cycloalkyl, $(C_3\text{-}C_6)$cycloalkyl-$(C_3\text{-}C_6)$cycloalkyl, $(C_1\text{-}C_4)$alkyl-$(C_3\text{-}C_6)$cycloalkyl, halo$(C_3\text{-}C_6)$cycloalkyl, $(C_1\text{-}C_4)$alkylthio-$(C_1\text{-}C_4)$alkyl, $(C_1\text{-}C_4)$alkylsulphinyl-$(C_1\text{-}C_4)$alkyl, $(C_1\text{-}C_4)$alkylsulphonyl-$(C_1\text{-}C_4)$alkyl or $(C_1\text{-}C_4)$alkylcarbonyl-$(C_1\text{-}C_4)$alkyl,
$R^7$ is $(C_1\text{-}C_4)$alkyl, $(C_1\text{-}C_4)$haloalkyl, $(C_1\text{-}C_4)$cyanoalkyl, $(C_1\text{-}C_4)$hydroxyalkyl, $(C_1\text{-}C_4)$alkoxy-$(C_1\text{-}C_4)$alkyl, $(C_1\text{-}C_4)$haloalkoxy-$(C_1\text{-}C_4)$alkyl, $(C_2\text{-}C_4)$alkenyl, $(C_2\text{-}C_4)$alkenyloxy-$(C_1\text{-}C_4)$alkyl, $(C_2\text{-}C_4)$haloalkenyloxy-$(C_1\text{-}C_4)$alkyl, $(C_2\text{-}C_4)$haloalkenyl, $(C_2\text{-}C_4)$cyanoalkenyl, $(C_2\text{-}C_4)$alkynyl, $(C_2\text{-}C_4)$alkynyloxy-$(C_1\text{-}C_4)$alkyl, $(C_2\text{-}C_4)$haloalkynyl, $(C_3\text{-}C_6)$cycloalkyl, $(C_3\text{-}C_6)$cycloalkyl-$(C_3\text{-}C_6)$cycloalkyl, $(C_1\text{-}C_4)$alkyl-$(C_3\text{-}C_6)$cycloalkyl, halo$(C_3\text{-}C_6)$cycloalkyl, $(C_1\text{-}C_4)$alkylthio-$(C_1\text{-}C_4)$alkyl, $(C_1\text{-}C_4)$alkylsulphinyl-$(C_1\text{-}C_4)$alkyl, $(C_1\text{-}C_4)$alkylsulphonyl-$(C_1\text{-}C_4)$alkyl or $(C_1\text{-}C_4)$alkylcarbonyl-$(C_1\text{-}C_4)$alkyl, and
A is hydrogen, cyano, halogen, $(C_1\text{-}C_4)$alkyl, $(C_1\text{-}C_4)$haloalkyl, $(C_2\text{-}C_4)$alkenyl, $(C_2\text{-}C_4)$haloalkenyl, $(C_2\text{-}C_4)$alkynyl, $(C_2\text{-}C_4)$haloalkynyl, $(C_3\text{-}C_6)$cycloalkyl, $(C_3\text{-}C_6)$cycloalkyl-$(C_3\text{-}C_6)$cycloalkyl, $(C_1\text{-}C_4)$alkyl-$(C_3\text{-}C_6)$cycloalkyl, $(C_1\text{-}C_4)$alkoxy, $(C_1\text{-}C_4)$haloalkoxy, $(C_1\text{-}C_4)$alkoxyimino, $(C_1\text{-}C_4)$alkylthio, $(C_1\text{-}C_4)$haloalkylthio, $(C_1\text{-}C_4)$alkylsulphinyl, $(C_1\text{-}C_4)$haloalkylsulphinyl, $(C_1\text{-}C_4)$alkylsulphonyl, $(C_1\text{-}C_4)$haloalkylsulphonyl, $(C_1\text{-}C_4)$alkylsulphonyloxy, $(C_1\text{-}C_4)$alkylcarbonyl, $(C_1\text{-}C_4)$haloalkylcarbonyl, aminocarbonyl, $(C_1\text{-}C_4)$alkylaminocarbonyl, di-$(C_1\text{-}C_4)$alkylaminocarbonyl, $(C_1\text{-}C_4)$alkylsulphonylamino, $(C_1\text{-}C_4)$alkylamino, di-$(C_1\text{-}C_4)$alkylamino, aminosulphonyl, $(C_1\text{-}C_4)$alkylaminosulphonyl or di-$(C_1\text{-}C_4)$alkylaminosulphonyl,
or A is —O—$CF_2$—O— and, together with $Q^1$ and the carbon atom to which it is bonded, forms a five-membered ring where $Q^1$ is carbon.

An alternative embodiment is that of compounds of the structure Q-H
in which (configuration Q-H-1-2)
Q is a structural element where the symbol # indicates the bond to the rest of the molecule and
$Q^1$ is N or $CR^6$,
$Q^2$ is N or $CR^6$,
$Q^3$ is N or C,
$Q^4$ is O, S, N or $NR^7$,
$Q^5$ is N or C,
$Q^6$ is N or CH,
$R^6$ is hydrogen, $(C_1\text{-}C_4)$alkyl, $(C_1\text{-}C_4)$haloalkyl, $(C_1\text{-}C_4)$cyanoalkyl, $(C_1\text{-}C_4)$hydroxyalkyl, $(C_1\text{-}C_4)$alkoxy-$(C_1\text{-}C_4)$alkyl, $(C_1\text{-}C_4)$haloalkoxy-$(C_1\text{-}C_4)$alkyl, $(C_2\text{-}C_4)$alkenyl, $(C_2\text{-}C_4)$alkenyloxy-$(C_1\text{-}C_4)$alkyl, $(C_2\text{-}C_4)$haloalkenyloxy-$(C_1\text{-}C_4)$alkyl, $(C_2\text{-}C_4)$haloalkenyl, $(C_2\text{-}C_4)$cyanoalkenyl, $(C_2\text{-}C_4)$alkynyl, $(C_2\text{-}C_4)$alkynyloxy-$(C_1\text{-}C_4)$alkyl, $(C_2\text{-}C_4)$haloalkynyl, $(C_3\text{-}C_6)$cycloalkyl, $(C_3\text{-}C_6)$cycloalkyl-$(C_3\text{-}C_6)$cycloalkyl, $(C_1\text{-}C_4)$alkyl-$(C_3\text{-}C_6)$cycloalkyl, halo$(C_3\text{-}C_6)$cycloalkyl, $(C_1\text{-}C_4)$alkylthio-$(C_1\text{-}C_4)$alkyl, $(C_1\text{-}C_4)$alkylsulphinyl-$(C_1\text{-}C_4)$alkyl, $(C_1\text{-}C_4)$alkylsulphonyl-$(C_1\text{-}C_4)$alkyl or $(C_1\text{-}C_4)$alkylcarbonyl-$(C_1\text{-}C_4)$alkyl,
$R^7$ is $(C_1\text{-}C_4)$alkyl, $(C_1\text{-}C_4)$haloalkyl, $(C_1\text{-}C_4)$cyanoalkyl, $(C_1\text{-}C_4)$hydroxyalkyl, $(C_1\text{-}C_4)$alkoxy-$(C_1\text{-}C_4)$alkyl, $(C_1\text{-}C_4)$haloalkoxy-$(C_1\text{-}C_4)$alkyl, $(C_2\text{-}C_4)$alkenyl, $(C_2\text{-}C_4)$alkenyloxy-$(C_1\text{-}C_4)$alkyl, $(C_2\text{-}C_4)$haloalkenyloxy-$(C_1\text{-}C_4)$alkyl, $(C_2\text{-}C_4)$haloalkenyl, $(C_2\text{-}C_4)$cyanoalkenyl, $(C_2\text{-}C_4)$alkynyl, $(C_2\text{-}C_4)$alkynyloxy-$(C_1\text{-}C_4)$alkyl, $(C_2\text{-}C_4)$haloalkynyl, $(C_3\text{-}C_6)$cycloalkyl, $(C_3\text{-}C_6)$cycloalkyl-$(C_3\text{-}C_6)$cycloalkyl, $(C_1\text{-}C_4)$alkyl-$(C_3\text{-}C_6)$cycloalkyl, halo$(C_3\text{-}C_6)$cycloalkyl, $(C_1\text{-}C_4)$alkylthio-$(C_1\text{-}C_4)$alkyl, $(C_1\text{-}C_4)$alkylsulphinyl-$(C_1\text{-}C_4)$alkyl, $(C_1\text{-}C_4)$alkylsulphonyl-$(C_1\text{-}C_4)$alkyl or $(C_1\text{-}C_4)$alkylcarbonyl-$(C_1\text{-}C_4)$alkyl, and
A is cyano, $(C_1\text{-}C_4)$alkyl, $(C_1\text{-}C_4)$haloalkyl, $(C_2\text{-}C_4)$alkenyl, $(C_2\text{-}C_4)$haloalkenyl, $(C_2\text{-}C_4)$alkynyl, $(C_2\text{-}C_4)$haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)alkoxyimino, ($C_1$-$C_4$)alkylthio, ($C_1$-$C_4$)haloalkylthio, ($C_1$-$C_4$)alkylsulphinyl, ($C_1$-$C_4$)haloalkylsulphinyl, ($C_1$-$C_4$)alkylsulphonyl, ($C_1$-$C_4$)haloalkylsulphonyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl or di-($C_1$-$C_4$)alkylaminosulphonyl, or A is —O—$CF_2$—O— and, together with $Q^1$ and the carbon atom to which it is bonded, forms a five-membered ring where $Q^1$ is carbon.

Preferably, $Q^1$, $Q^2$, $Q^3$, $Q^4$, $Q^5$ and $Q^6$ in configuration Q-H-1-1 and configuration Q-H-1-2 represent not more than five nitrogen atoms overall and further preferably not more than four nitrogen atoms overall.

Preferred (configuration Q-H-2-1 and Q-H-2-2), particularly preferred (configuration Q-H-3-1) and very particularly preferred (configuration Q-H-4-1) definitions of the radicals included in the compounds Q-H mentioned in the above configurations Q-H-1-1 and Q-H-1-2 are elucidated hereinafter.

Configuration Q-H-2-1:
Q is preferably a structural element from the group of Q1 to Q15
$R^7$ is preferably ($C_1$-$C_4$)alkyl, ($C_1$-$C_4$)haloalkyl, ($C_1$-$C_4$)alkoxy-($C_1$-$C_4$)alkyl, ($C_1$-$C_4$)haloalkoxy-($C_1$-$C_4$)alkyl, ($C_1$-$C_4$)alkylthio-($C_1$-$C_4$)alkyl, ($C_1$-$C_4$)alkylsulphinyl-($C_1$-$C_4$)alkyl, ($C_1$-$C_4$)alkylsulphonyl-($C_1$-$C_4$)alkyl or ($C_1$-$C_4$)alkylcarbonyl-($C_1$-$C_4$)alkyl, and
A is preferably fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulphinyl or trifluoromethylsulphonyl.

Configuration Q-H-2-2:
Q is preferably a structural element from the group of Q1 to Q15
$R^7$ is preferably ($C_1$-$C_4$)alkyl, ($C_1$-$C_4$)haloalkyl, ($C_1$-$C_4$)alkoxy-($C_1$-$C_4$)alkyl, ($C_1$-$C_4$)haloalkoxy-($C_1$-$C_4$)alkyl, ($C_1$-$C_4$)alkylthio-($C_1$-$C_4$)alkyl, ($C_1$-$C_4$)alkylsulphinyl-($C_1$-$C_4$)alkyl, ($C_1$-$C_4$)alkylsulphonyl-($C_1$-$C_4$)alkyl or ($C_1$-$C_4$)alkylcarbonyl-($C_1$-$C_4$)alkyl, and
A is preferably fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulphinyl or trifluoromethylsulphonyl.

Configuration Q-H-3-1:
Q is more preferably a structural element from the group of Q2, Q3, Q10, Q12, Q14 and Q15
$R^7$ is more preferably ($C_1$-$C_4$)alkyl or ($C_1$-$C_4$)alkoxy-($C_1$-$C_4$)alkyl, and
A is more preferably trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethylthio, trifluoromethylsulphinyl or trifluoromethylsulphonyl.

Configuration Q-H-4-1:
Q is most preferably the structural element Q3 or Q14,
$R^7$ is most preferably methyl, ethyl, n-propyl or isopropyl, especially methyl, and
A is most preferably trifluoromethyl.

The radical definitions given above can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

Very particular preference is given in accordance with the invention to those compounds in which there is a combination of the definitions listed above as being most preferred.

One example of such a very particularly preferred compound is:

Q-X-1:

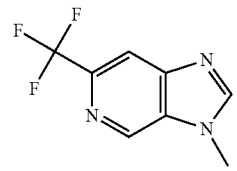

3-methyl-6-(trifluoromethyl)-3H-imidazo[4,5-c]pyridine

Q-X-2:

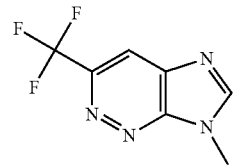

7-methyl-3-(trifluoromethyl)-7H-imidazo[4,5-c]pyridazine

The present invention further provides compounds of the formula (IIIa)

(IIIa)

in which
Q is a structural element

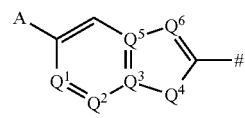

where the symbol # indicates the bond to the rest of the molecule and $Q^1$ is N or $CR^6$,
$Q^2$ is N or $CR^6$,
$Q^3$ is N or C,
$Q^4$ is O, S, N or $NR^7$,
$Q^5$ is N or C,
$Q^6$ is N or CH,
$R^6$ is hydrogen, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylthio-($C_1$-$C_4$)alkyl, ($C_1$-$C_4$)alkylsulphinyl-($C_1$-$C_4$)alkyl, ($C_1$-$C_4$)alkylsulphonyl-($C_1$-$C_4$)alkyl or ($C_1$-$C_4$)alkylcarbonyl-($C_1$-$C_4$)alkyl,
$R^7$ is ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylthio-($C_1$-$C_4$)alkyl, ($C_1$-$C_4$)alkylsulphinyl-($C_1$-$C_4$)alkyl, ($C_1$-$C_4$)alkylsulphonyl-($C_1$-$C_4$)alkyl or ($C_1$-$C_4$)alkylcarbonyl-($C_1$-$C_4$)alkyl,
A is hydrogen, cyano, halogen, ($C_1$-$C_4$)alkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)alkoxyimino, ($C_1$-$C_4$)alkylthio, ($C_1$-$C_4$)haloalkylthio, ($C_1$-$C_4$)alkylsulphinyl, ($C_1$-$C_4$)haloalkylsulphinyl, ($C_1$-$C_4$)alkylsulphonyl, ($C_1$-$C_4$)haloalkylsulphonyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl or di-($C_1$-$C_4$)alkylaminosulphonyl,
or A is —O—$CF_2$—O— and, together with $Q^1$ and the carbon atom to which it is bonded, forms a five-membered ring where $Q^1$ is carbon, and
$R^2$ is halogen or —O-pivaloyl.

Preferably, $Q^1$, $Q^2$, $Q^3$, $Q^4$, $Q^5$ and $Q^6$ represent not more than five nitrogen atoms overall and further preferably not more than four nitrogen atoms overall.

Preferred, particularly preferred and very particularly preferred definitions of the radicals included in the aforementioned compounds of the formula (IIIa) are elucidated hereinafter.

Q is preferably a structural element from the group of Q1 to Q15

$R^7$ is preferably ($C_1$-$C_4$)alkyl, ($C_1$-$C_4$)haloalkyl, ($C_1$-$C_4$)alkoxy-($C_1$-$C_4$)alkyl, ($C_1$-$C_4$)haloalkoxy-($C_1$-$C_4$)alkyl, ($C_1$-$C_4$)alkylthio-($C_1$-$C_4$)alkyl, ($C_1$-$C_4$)alkylsulphinyl-($C_1$-$C_4$)alkyl, ($C_1$-$C_4$)alkylsulphonyl-($C_1$-$C_4$)alkyl or ($C_1$-$C_4$)alkylcarbonyl-($C_1$-$C_4$)alkyl, A is preferably fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulphinyl or trifluoromethylsulphonyl, and $R^2$ is preferably halogen, especially chlorine, bromine or iodine.

Q is more preferably a structural element from the group of Q2, Q3, Q10, Q12, Q14 and Q15

$R^7$ is more preferably ($C_1$-$C_4$)alkyl or ($C_1$-$C_4$)alkoxy-($C_1$-$C_4$)alkyl, A is more preferably trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethylthio, trifluoromethylsulphinyl or trifluoromethylsulphonyl, and $R^2$ is more preferably chlorine.

Q is most preferably the structural element Q3 or Q14, $R^7$ is most preferably methyl, ethyl, n-propyl or isopropyl, especially methyl, A is most preferably trifluoromethyl, and $R^2$ is most preferably chlorine.

The radical definitions given above can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

Very particular preference is given in accordance with the invention to those compounds in which there is a combination of the definitions listed above as being most preferred.

The compounds of the formula (IIIa) may also be present on their own or as the alkali metal or alkaline earth metal halide complex, preferably as the lithium chloride complex.

Examples of such very particularly preferred compounds are:

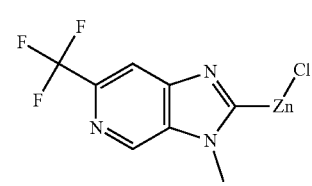

chloro[3-methyl-6-(trifluoromethyl)-3H-imidazo[4,5-c]pyridin-2-yl]zinc

IIIa-1

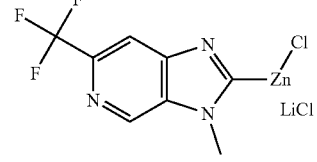

chloro[3-methyl-6-(trifluoromethyl)-3H-imidazo[4,5-c]pyridin-2-yl]zinc lithium chloride complex -continued

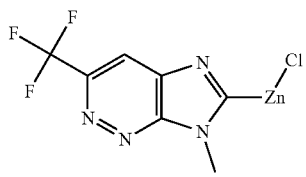

chloro[3-methyl-6-(trifluoromethyl)-3H-imidazo[4,5-c]pyridazin-2-yl]zinc

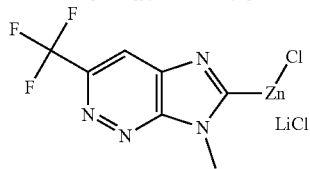

chloro[3-methyl-6-(trifluoromethyl)-3H-imidazo[4,5-c]pyridazin-2-yl]zinc lithium chloride complex The present invention further provides compounds of the formula (IIIb)

Q-Zn-Q  (IIIb)

in which
Q is a structural element

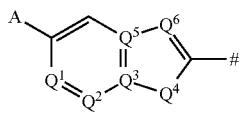

where the symbol # indicates the bond to the rest of the molecule and
$Q^1$ is N or $CR^6$,
$Q^2$ is N or $CR^6$,
$Q^3$ is N or C,
$Q^4$ is O, S, N or $NR^7$,
$Q^5$ is N or C,
$Q^6$ is N or CH,
$R^6$ is hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl,
$R^7$ is $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, and A is hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$alkoxyimino, $(C_1-C_4)$alkylthio, $(C_1-C_4)$haloalkylthio, $(C_1-C_4)$alkylsulphinyl, $(C_1-C_4)$haloalkylsulphinyl, $(C_1-C_4)$alkylsulphonyl, $(C_1-C_4)$haloalkylsulphonyl, $(C_1-C_4)$alkylsulphonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulphonylamino, $(C_1-C_4)$alkylamino, di-$(C_1-C_4)$alkylamino, aminosulphonyl, $(C_1-C_4)$alkylaminosulphonyl or di-$(C_1-C_4)$alkylaminosulphonyl,
or A is —O—$CF_2$—O— and, together with $Q^1$ and the carbon atom to which it is bonded, forms a five-membered ring where $Q^1$ is carbon.
Preferably, $Q^1$, $Q^2$, $Q^3$, $Q^4$, $Q^5$ and $Q^6$ represent not more than five nitrogen atoms overall and further preferably not more than four nitrogen atoms overall.

Preferred, particularly preferred and very particularly preferred definitions of the radicals included in the aforementioned compounds of the formula (IIIb) are elucidated hereinafter.

Q is preferably a structural element from the group of Q1 to Q15

$R^7$ is preferably $(C_1-C_4)$alkyl, $(C_1-C_4)$haloalkyl, $(C_1-C_4)$alkoxy-$(C_1-C_4)$alkyl, $(C_1-C_4)$haloalkoxy-$(C_1-C_4)$alkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, and A is preferably fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoroethylsulphinyl or trifluoromethylsulphonyl.

Q is more preferably a structural element from the group of Q2, Q3, Q10, Q12, Q14 and Q15

$R^7$ is more preferably $(C_1-C_4)$alkyl or $(C_1-C_4)$alkoxy-$(C_1-C_4)$alkyl, and A is more preferably trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethylthio, trifluoromethylsulphinyl or trifluoromethylsulphonyl.

Q is most preferably the structural element Q3 or Q14,
$R^7$ is most preferably methyl, ethyl, n-propyl or isopropyl, especially methyl, and
A is most preferably trifluoromethyl.

The radical definitions given above can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

Very particular preference is given in accordance with the invention to those compounds in which there is a combination of the definitions listed above as being most preferred.

The compounds of the formula (IIIb) may also be present on their own or as the alkali metal or alkaline earth metal halide complex, preferably as the lithium chloride complex.

The present invention further provides compounds of the formula (II)

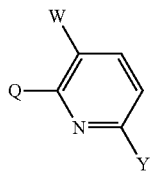

in which (configuration II-1-1)
Q is a structural element

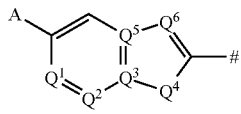

where the symbol # indicates the bond to the rest of the molecule and
$Q^1$ is N or $CR^6$,
$Q^2$ is N or $CR^6$,
$Q^3$ is N or C,
$Q^4$ is O, S, N or $NR^7$,
$Q^5$ is N or C,
$Q^6$ is N or CH,
$R^6$ is hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl,
$R^7$ is $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl,
A is hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$alkoxyimino, $(C_1-C_4)$alkylthio, $(C_1-C_4)$haloalkylthio, $(C_1-C_4)$alkylsulphinyl, $(C_1-C_4)$haloalkylsulphinyl, $(C_1-C_4)$alkylsulphonyl, $(C_1-C_4)$haloalkylsulphonyl, $(C_1-C_4)$alkylsulphonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulphonylamino, $(C_1-C_4)$alkylamino, di-$(C_1-C_4)$alkylamino, aminosulphonyl, $(C_1-C_4)$alkylaminosulphonyl or di-$(C_1-C_4)$alkylaminosulphonyl,
or A is —O—$CF_2$—O— and, together with $Q^1$ and the carbon atom to which it is bonded, forms a five-membered ring where $Q^1$ is carbon,
W is halogen, and
Y is halogen, $CO_2R^1$ or $NO_2$, where $R^1$ is $(C_1-C_6)$-alkyl or $(C_1-C_6)$-haloalkyl.

An alternative embodiment (configuration II-1-2) is that of compounds of the formula (II) in which
Q is a structural element

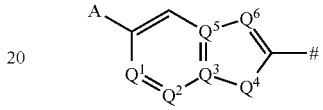

where the symbol # indicates the bond to the rest of the molecule and
$Q^1$ is N or $CR^6$,
$Q^2$ is N or $CR^6$,
$Q^3$ is N or C,
$Q^4$ is O, S, N or $NR^7$,
$Q^5$ is N or C,
$Q^6$ is N or CH,
$R^6$ is hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl,
$R^7$ is $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl,
A is hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$alkoxyimino, $(C_1-C_4)$alkylthio, $(C_1-C_4)$haloalkylthio, $(C_1-C_4)$alkylsulphinyl, $(C_1-C_4)$haloalkylsulphinyl, $(C_1-C_4)$alkylsulphonyl, $(C_1-C_4)$haloalkylsulphonyl, $(C_1-C_4)$alkylsulphonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulphonylamino, ($C_1$-$C_4$)alkylamino, di-($C_1$-$C_4$)alkylamino, aminosulphonyl, ($C_1$-$C_4$)alkylaminosulphonyl or di-($C_1$-$C_4$)alkylaminosulphonyl, or A is —O—CF$_2$—O— and, together with Q$^1$ and the carbon atom to which it is bonded, forms a five-membered ring where Q$^1$ is carbon, W is fluorine or bromine, and Y is halogen, CO$_2$R$^1$ or NO$_2$, where R$^1$ is ($C_1$-$C_6$)-alkyl or ($C_1$-$C_6$)-haloalkyl.

Preferably, Q$^1$, Q$^2$, Q$^3$, Q$^4$, Q$^5$ and Q$^6$ in configuration II-1-1 and configuration II-1-2 represent not more than five nitrogen atoms overall and further preferably not more than four nitrogen atoms overall.

Preferred (configurations II-2-1 and II-2-2), particularly preferred (configurations II-3-1 and II-3-2) and very particularly preferred (configuration II-4-1) definitions of the radicals included in the aforementioned formula (II) are elucidated hereinafter.

Configuration II-2-1:

Q is preferably a structural element from the group of Q1 to Q15

R$^7$ is preferably ($C_1$-$C_4$)alkyl, ($C_1$-$C_4$)haloalkyl, ($C_1$-$C_4$)alkoxy-($C_1$-$C_4$)alkyl, ($C_1$-$C_4$)haloalkoxy-($C_1$-$C_4$)alkyl, ($C_1$-$C_4$)alkylthio-($C_1$-$C_4$)alkyl, ($C_1$-$C_4$)alkylsulphinyl-($C_1$-$C_4$)alkyl, ($C_1$-$C_4$)alkylsulphonyl-($C_1$-$C_4$)alkyl or ($C_1$-$C_4$)alkylcarbonyl-($C_1$-$C_4$)alkyl, A is preferably fluorine, chlorine, bromine, fluoromethyl, difluoromethyl, trifluoromethyl, fluoroethyl (CH$_2$CFH$_2$, CHFCH$_3$), difluoroethyl (CF$_2$CH$_3$, CH$_2$CHF$_2$, CHFCFH$_2$), trifluoroethyl, (CH$_2$CF$_3$, CHFCHF$_2$, CF$_2$CFH$_2$), tetrafluoroethyl (CHFCF$_3$, CF$_2$CHF$_2$), pentafluoroethyl, trifluoromethoxy, difluorochloromethoxy, dichlorofluoromethoxy, trifluoromethylthio, trifluoromethylsulphinyl or trifluoromethylsulphonyl, W is preferably fluorine or bromine, and Y is preferably fluorine, chlorine, bromine, CO$_2$R$^1$ or NO$_2$, where R$^1$ is ($C_1$-$C_4$)-alkyl.

Configuration II-2-2:

Q is preferably a structural element from the group of Q1 to Q15

R$^7$ is preferably ($C_1$-$C_4$)alkyl, ($C_1$-$C_4$)haloalkyl, ($C_1$-$C_4$)alkoxy-($C_1$-$C_4$)alkyl, ($C_1$-$C_4$)haloalkoxy-($C_1$-$C_4$)alkyl, ($C_1$-$C_4$)alkylthio-($C_1$-$C_4$)alkyl, ($C_1$-$C_4$)alkylsulphinyl-($C_1$-$C_4$)alkyl, ($C_1$-$C_4$)alkylsulphonyl-($C_1$-$C_4$)alkyl or ($C_1$-$C_4$)alkylcarbonyl-($C_1$-$C_4$)alkyl, A is preferably fluorine, chlorine, bromine, fluoromethyl, difluoromethyl, trifluoromethyl, fluoroethyl (CH$_2$CFH$_2$, CHFCH$_3$), difluoroethyl (CF$_2$CH$_3$, CH$_2$CHF$_2$, CHFCFH$_2$), trifluoroethyl, (CH$_2$CF$_3$, CHFCHF$_2$, CF$_2$CFH$_2$), tetrafluoroethyl (CHFCF$_3$, CF$_2$CHF$_2$), pentafluoroethyl, trifluoromethoxy, difluorochloromethoxy, dichlorofluoromethoxy, trifluoromethylthio, trifluoromethylsulphinyl or trifluoromethylsulphonyl, W is preferably fluorine or bromine, and Y is preferably fluorine, chlorine, bromine, CO$_2$R$^1$ or NO$_2$, where R$^1$ is ($C_1$-$C_4$)-alkyl.

Configuration II-3-1:

Q is more preferably a structural element from the group of Q2, Q3, Q10, Q12, Q14 and Q15

R$^7$ is more preferably ($C_1$-$C_4$)alkyl or ($C_1$-$C_4$)alkoxy-($C_1$-$C_4$)alkyl, A is more preferably trifluoromethyl, fluoroethyl (CH$_2$CFH$_2$, CHFCH$_3$), difluoroethyl (CF$_2$CH$_3$, CH$_2$CHF$_2$, CHFCFH$_2$), trifluoroethyl, (CH$_2$CF$_3$, CHFCHF$_2$, CF$_2$CFH$_2$), tetrafluoroethyl (CHFCF$_3$, CF$_2$CHF$_2$), pentafluoroethyl, trifluoromethylthio, trifluoromethylsulphinyl or trifluoromethylsulphonyl, W is more preferably fluorine or chlorine, especially fluorine, and Y is more preferably chlorine, bromine, CO$_2$R$^1$ or NO$_2$, where R$^1$ is ($C_1$-$C_4$)-alkyl.

Configuration II-3-2:

Q is more preferably a structural element from the group of Q2, Q3, Q10, Q12, Q14 and Q15

R$^7$ is more preferably ($C_1$-$C_4$)alkyl or ($C_1$-$C_4$)alkoxy-($C_1$-$C_4$)alkyl, A is more preferably trifluoromethyl, fluoroethyl (CH$_2$CFH$_2$, CHFCH$_3$), difluoroethyl (CF$_2$CH$_3$, CH$_2$CHF$_2$, CHFCFH$_2$), trifluoroethyl, (CH$_2$CF$_3$, CHFCHF$_2$, CF$_2$CFH$_2$), tetrafluoroethyl (CHFCF$_3$, CF$_2$CHF$_2$), pentafluoroethyl, trifluoromethylthio, trifluoromethylsulphinyl or trifluoromethylsulphonyl, W is more preferably fluorine, and Y is more preferably chlorine, bromine, CO$_2$R$^1$ or NO$_2$, where R$^1$ is ($C_1$-$C_4$)-alkyl.

Configuration II-4-1:

Q is most preferably the structural element Q3 or Q14,

R$^7$ is most preferably methyl, ethyl, n-propyl or isopropyl, especially methyl, A is most preferably trifluoromethyl, W is most preferably fluorine, and Y is most preferably chlorine, bromine, CO$_2$R$^1$ or NO$_2$, where R$^1$ is methyl.

The radical definitions given above can be combined with one another as desired, i.e. including combinations between the respective ranges of preference.

Preference is given in accordance with the invention to those compounds in which there is a combination of the definitions listed above as being preferred.

Particular preference is given in accordance with the invention to those compounds in which there is a combination of the definitions listed above as being more preferred.

Very particular preference is given in accordance with the invention to those compounds in which there is a combination of the definitions listed above as being most preferred.

Examples of such very particularly preferred compounds are:

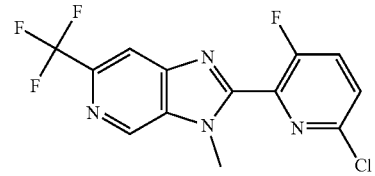 [SMILES: Cn1c(-c2nc(Cl)ccc2F)nc2cc(C(F)(F)F)ncc21]

2-(6-Chloro-3-fluoropyridin-2-yl)-3-methyl-6-(trifluoromethyl)-3H-imidazo[4,5-c]pyridine

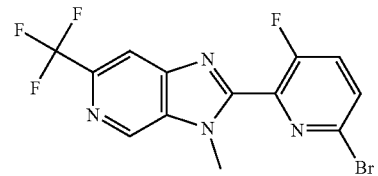 [SMILES: Cn1c(-c2nc(Br)ccc2F)nc2cc(C(F)(F)F)ncc21]

2-(6-Bromo-3-fluoropyridin-2-yl)-3-methyl-6-(trifluoromethyl)-3H-imidazo[4,5-c]pyridine

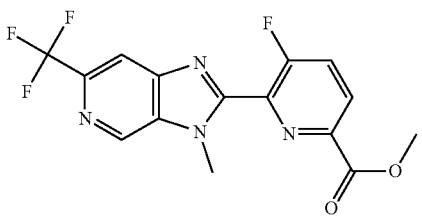 [SMILES: COC(=O)c1ccc(F)c(-c2nc3cc(C(F)(F)F)ncc3n2C)n1]

Methyl 5-fluoro-6-[3-methyl-6-(trifluoromethyl)-3H-imidazo[4,5-c]pyridine-2-yl]pyridine-2-carboxylate

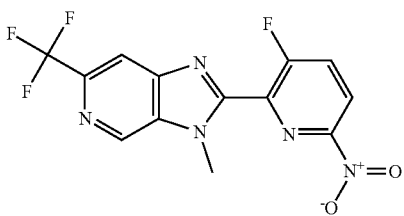

2-(3-Fluoro-6-nitropyridin-2-yl)-3-methyl-6-(trifluoromethyl)-3H-imidazo[4,5-c]pyridine

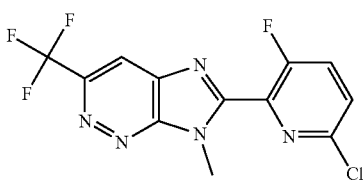 [SMILES: Cn1c(-c2nc(Br)ccc2F)nc2cc(C(F)(F)F)nnc21]

6-(6-Chloro-3-fluoropyridin-2-yl)-7-methyl-3-(trifluoromethyl)-7H-imidazo[4,5-c]pyridazine

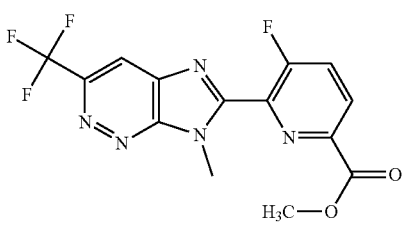

Methyl 5-fluoro-6-[7-methyl-3-(trifluoromethyl)-7H-imidazo[4,5-c]pyridazin-6-yl]pyridine-2-carboxylate

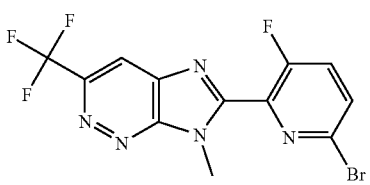

6-(6-Bromo-3-fluoropyridin-2-yl)-7-methyl-3-(trifluoromethyl)-7H-imidazo[4,5-c]pyridazine The present invention is elucidated in detail by the examples which follow, although the examples should not be interpreted in such a manner that they restrict the invention.

Example 1

Synthesis of 3-methyl-6-(trifluoromethyl)-3H-imidazo[4,5-c]pyridine

N3-Methyl-6-(trifluoromethyl)pyridine-3,4-diamine (500 mg, 2.6 mmol), dissolved in formic acid (4 ml, 106 mmol), was heated with microwaves at 150° C. for 1 hour. After customary workup by addition of saturated aqueous ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), 3-methyl-6-(trifluoromethyl)-3H-imidazo[4,5-c]pyridine (480 mg, 91%) was obtained as a white solid. HPLC-MS: log P=1.09; Mass (m/z+1): 202.0; 1HNMR (D6-DMSO): δ 9.14 (s, 1H), 8.61 (s, 1H), 8.19 (s, 1H), 4.02 (s, 3H).

Example 2

Synthesis of 2-(6-chloro-3-fluoropyridin-2-yl)-3-methyl-6-(trifluoromethyl)-3H-imidazo[4,5-c]pyridine

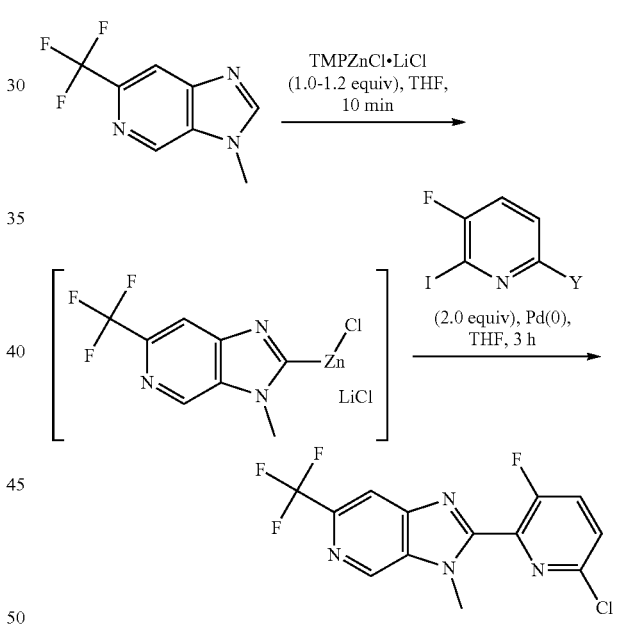

To 3-methyl-6-(trifluoromethyl)-3H-imidazo[4,5-c]pyridine (201 mg, 1.0 mmol), dissolved in THF (2 ml), was added TMPZnCl.LiCl (1.31 M in THF, 0.84 ml, 1.1 mmol) at 25° C. under argon; this reaction solution was stirred for 10 min. Subsequently, 6-chloro-3-fluoro-2-iodopyridine (515 mg, 2 mmol in 4 ml THF) and tetrakis(triphenylphosphine)palladium(0) (115 mg, 0.1 mmol) were added at 25° C. and the solution was stirred at 65° C. for a further 3 hours. After customary workup by addition of saturated aqueous ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), 2-(6-chloro-3-fluoropyridin-2-yl)-3-methyl-6-(trifluoromethyl)-3H-imidazo[4,5-c]pyridine (177 mg, 52%) was obtained as a white solid. HPLC-MS: log P=2.38; Mass (m/z): 331.0; 1HNMR (D6-DMSO): δ 9.29 (s, 1H), 8.32 (s, 1H), 8.19 (t, 1H), 7.91 (dd, 1H), 4.14 (s, 3H).

Example 3

Synthesis of methyl 5-fluoro-6-[3-methyl-6-(trifluoromethyl)-3H-imidazo[4,5-c]pyridin-2-yl]pyridine-2-carboxylate To 3-methyl-6-(trifluoromethyl)-3H-imidazo[4,5-c]pyridine (201 mg, 1.0 mmol), dissolved in THF (2 ml), was added TMPZnCl.LiCl (1.31 M in THF, 0.84 ml, 1.1 mmol) at 25° C. under argon; this reaction solution was stirred for 10 min. Subsequently, methyl 5-fluoro-6-iodopyridine-2-carboxylate (562 mg, 2 mmol in 4 ml THF) and tetrakis(triphenylphosphine)palladium(0) (115 mg, 0.1 mmol) were added at 25° C. and the solution was stirred at 65° C. for a further 3 hours. After customary workup by addition of saturated aqueous ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), methyl 5-fluoro-6-[3-methyl-6-(trifluoromethyl)-3H-imidazo[4,5-c]pyridin-2-yl]pyridine-2-carboxylate (160 mg, 45%) was obtained as a white solid. HPLC-MS: log P==2.03; Mass (m/z+1): 355.1; 1HNMR (D6-DMSO): 9.30 (s, 1H), 8.38 (dd, 1H), 8.34 (s, 1H), 8.24 (dd, 1H), 4.19 (s, 3H), 3.93 (s, 3H).

Example 4

Synthesis of 2-(6-bromo-3-fluoropyridin-2-yl)-3-methyl-6-(trifluoromethyl)-3H-imidazo[4,5-c]pyridine To 3-methyl-6-(trifluoromethyl)-3H-imidazo[4,5-c]pyridine (100 mg, 0.5 mmol), dissolved in THF (2 ml), was added TMPZnCl.LiCl (1.31 M in THF, 0.52 ml, 0.55 mmol) at 25° C. under argon; this reaction solution was stirred for 10 min. Subsequently, 6-bromo-3-fluoro-2-iodopyridine (301 mg, 1 mmol in 2 ml THF) and tetrakis(triphenylphosphine)palladium(0) (58 mg, 0.05 mmol) were added at 25° C. and the solution was stirred at 65° C. for a further 3 hours. After customary workup by addition of saturated aqueous ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), 2-(6-bromo-3-fluoropyridin-2-yl)-3-methyl-6-(trifluoromethyl)-3H-imidazo[4,5-c]pyridine (101 mg, 54%) was obtained as a white solid. HPLC-MS: log P=2.51; Mass (m/z+1): 376.9; 1HNMR (D6-DMSO): δ 9.29 (s, 1H), 8.33 (s, 1H), 8.05 (m, 2H), 4.13 (s, 3H).

Example 5

Synthesis of 7-methyl-3-(trifluoromethyl)-7H-imidazo[4,5-c]pyridazine

N3-Methyl-6-(trifluoromethyl)pyridazine-3,4-diamine (192 mg, 1.0 mmol), dissolved in formic acid (0.4 ml, 106 mmol), was heated with microwaves at 150° C. for 2 hours. After customary workup by addition of saturated aqueous ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), 7-methyl-3-(trifluoromethyl)-7H-imidazo[4,5-c]pyridazine (149 mg, 74%) was obtained as a white solid. HPLC-MS: log P=0.95; Mass (m/z+1): 203.1; 1HNMR (D6-DMSO): δ 8.97 (s, 1H), 8.62 (s, 1H), 4.08 (s, 3H).

Example 6

Synthesis of 6-(6-chloro-3-fluoropyridin-2-yl)-7-methyl-3-(trifluoromethyl)-7H-imidazo[4,5-c]pyridazine To 7-methyl-3-(trifluoromethyl)-7H-imidazo[4,5-c]pyridazine (202 mg, 1.0 mmol), dissolved in THF (2 ml), was added TMPZnCl.LiCl (1.31 M in THF, 0.84 ml, 1.1 mmol) at 25° C. under argon; this reaction solution was stirred for 10 min. Subsequently, 6-chloro-3-fluoro-2-iodopyridine (515 mg, 2 mmol in 4 ml THF) and tetrakis(triphenylphosphine)palladium(0) (115 mg, 0.1 mmol) were added at 25° C. and the solution was stirred at 65° C. for a further 3 hours. After customary workup by addition of saturated aqueous ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), 6-(6-chloro-3-fluoropyridin-2-yl)-7-methyl-3-(trifluoromethyl)-7H-imidazo[4,5-c]pyridazine (125 mg, 38%) was obtained as a white solid. HPLC-MS: log P=2.46; Mass (m/z): 332.0; 1HNMR (D6-DMSO): δ 8.77 (s, 1H), 8.23 (t, 1H), 7.98 (dd, 1H), 4.25 (s, 3H).

Example 7

Synthesis of methyl 5-fluoro-6-[7-methyl-3-(trifluoromethyl)-7H-imidazo[4,5-c]pyridazin-6-yl]pyridine-2-carboxylate To 7-methyl-3-(trifluoromethyl)-7H-imidazo[4,5-c]pyridazine (202 mg, 1.0 mmol), dissolved in THF (2 ml), was added TMPZnCl.LiCl (1.31 M in THF, 0.84 ml, 1.1 mmol) at 25° C. under argon; this reaction solution was stirred for 10 min. Subsequently, methyl 5-fluoro-6-iodopyridine-2-carboxylate (562 mg, 2 mmol in 4 ml THF) and tetrakis(triphenylphosphine)palladium(0) (115 mg, 0.1 mmol) were added at 25° C. and the solution was stirred at 65° C. for a further 3 hours. After customary workup by addition of saturated aqueous ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), methyl 5-fluoro-6-[7-methyl-3-(trifluoromethyl)-7H-imidazo[4,5-c]pyridazin-6-yl]pyridine-2-carboxylate (208 mg, 59%) was obtained as a white solid. HPLC-MS: log P==2.09; Mass (m/z+1): 356.0; 1HNMR (D6-DMSO): 8.78 (s, 1H), 8.43 (dd, 1H), 8.28 (t, 1H), 4.32 (s, 3H), 3.96 (s, 3H).

Example 8

Synthesis of 6-(6-bromo-3-fluoropyridin-2-yl)-7-methyl-3-(trifluoromethyl)-7H-imidazo[4,5-c]pyridazine To 7-methyl-3-(trifluoromethyl)-7H-imidazo[4,5-c]pyridazine (340 mg, 1.7 mmol), dissolved in THF (2 ml), was added TMPZnCl.LiCl (1.31 M in THF, 1.41 ml, 1.85 mmol) at 25° C. under argon; this reaction solution was stirred for 10 min. Subsequently, 6-bromo-3-fluoro-2-iodopyridine (1.016 g, 3.36 mmol in 4 ml THF) and tetrakis(triphenylphosphine)palladium(0) (195 mg, 0.16 mmol) were added at 25° C. and the solution was stirred at 65° C. for a further 3 hours. After customary workup by addition of saturated aqueous ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), 6-(6-bromo-3-fluoropyridin-2-yl)-7-methyl-3-(trifluoromethyl)-7H-imidazo[4,5-c]pyridazine (408 mg, 62%) was obtained as a white solid. HPLC-MS: log P=2.58; Mass (m/z+1): 375.9; 1HNMR (D6-DMSO): δ 8.77 (s, 1H), 8.10 (m, 2H), 4.25 (s, 3H)

The invention claimed is:

1. Process for preparing compound of formula (II)

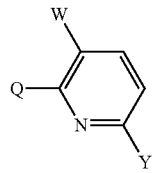

(II)

in which

Q is a structural element

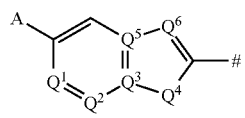

where the symbol # indicates the bond to the rest of the molecule and $Q^1$ is N or $CR^6$,
$Q^2$ is N or $CR^6$,
$Q^3$ is N or C,
$Q^4$ is O, S, N or $NR^7$,
$Q^5$ is N or C,
$Q^6$ is N or CH,
$R^6$ is hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, $R^7$ is $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, and A is hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$alkoxyimino, $(C_1-C_4)$alkylthio, $(C_1-C_4)$haloalkylthio, $(C_1-C_4)$alkylsulphinyl, $(C_1-C_4)$haloalkylsulphinyl, $(C_1-C_4)$alkylsulphonyl, $(C_1-C_4)$haloalkylsulphonyl, $(C_1-C_4)$alkylsulphonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulphonylamino, $(C_1-C_4)$alkylamino, di-$(C_1-C_4)$alkylamino, aminosulphonyl, $(C_1-C_4)$alkylaminosulphonyl or di-$(C_1-C_4)$alkylaminosulphonyl, or A is $-O-CF_2-O-$ and, together with $Q^1$ and the carbon atom to which it is bonded, forms a five-membered ring where $Q^1$ is carbon, W is halogen, and Y is halogen, $CO_2R^1$ or $NO_2$, where $R^1$ is $(C_1-C_6)$-alkyl or $(C_1-C_6)$-haloalkyl, wherein, first a), a compound Q-H in which Q is as defined above is reacted with an organozinc base of the structure $(NR^3R^4)-Zn-R^2$ or $(NR^3R^4)_2-Zn$ in which $R^2$ is halogen or $-O$-pivaloyl and $R^3$ and $R^4$ together form a $-(CH_2)_4-$, $-(CH_2)_5-$ or $-(CH_2)_2O(CH_2)_2-$ group, where each of these groups may optionally be substituted by 1, 2, 3 or 4 $R^5$ radicals and $R^5$ is selected from the group consisting of methyl, ethyl, n-propyl and i-propyl, to give a compound of formula (IIIa) or formula (IIIb)

in which Q and $R^2$ each have the definitions given above, and said compound of formula (IIIa) or (IIIb) is reacted in b) with a compound of formula (I)

in which X is halogen and W and Y each have the definitions given above, in the presence of a catalyst, to give the compound of formula (II).

2. Process according to claim 1, wherein
Q is a structural element from the group of Q1 to Q15

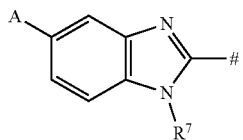 Q1

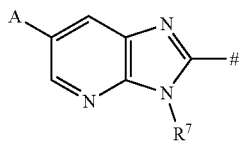 Q2

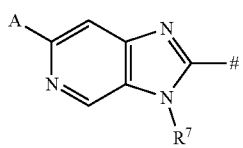 Q3

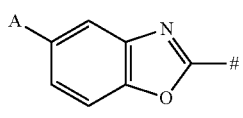 Q4

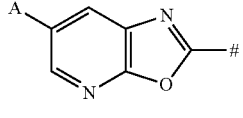 Q5

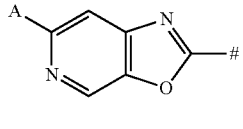 Q6

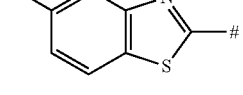 Q7

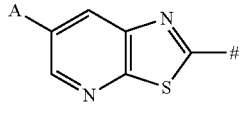 Q8

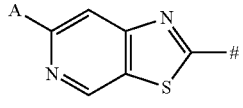 Q9

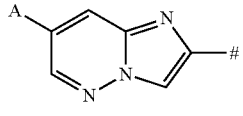 Q10

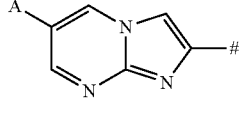 Q11

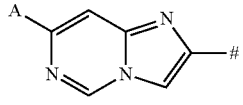 Q12

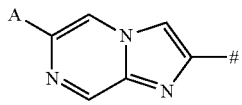 Q13

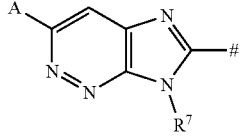 Q14

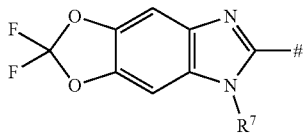 Q15

$R^7$ is $(C_1-C_4)$alkyl, $(C_1-C_4)$haloalkyl, $(C_1-C_4)$alkoxy-$(C_1-C_4)$alkyl, $(C_1-C_4)$haloalkoxy-$(C_1-C_4)$alkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, A is fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulphinyl or trifluoromethylsulphonyl, W is fluorine, chlorine or bromine, $R^2$ is halogen, X is halogen, and Y is fluorine, chlorine, bromine, $CO_2R$ or $NO_2$, where $R^1$ is $(C_1-C_4)$-alkyl.

3. Process according to claim 1, wherein
Q is a structural element from the group of Q2, Q3, Q10, Q12, Q14 and Q15
$R^7$ is $(C_1-C_4)$alkyl or $(C_1-C_4)$alkoxy-$(C_1-C_4)$alkyl,
A is trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethylthio, trifluoromethylsulphinyl or trifluoromethylsulphonyl,
W is fluorine or chlorine,
$R^2$ is chlorine,
X is bromine or iodine, and
Y is chlorine, bromine, $CO_2R^1$ or $NO_2$, where $R^1$ is $(C_1-C_4)$-alkyl.

4. Process according to claim 1, wherein
Q is the structural element Q3 or Q14
$R^7$ is methyl, ethyl, n-propyl or isopropyl,
A is trifluoromethyl,
W is fluorine,
$R^2$ is chlorine,
X is iodine, and
Y is chlorine, bromine, $CO_2R$ or $NO_2$, where $R^1$ is methyl.

5. Process according to claim 1, wherein
$R^3$ and $R^4$ together form a —$(CH_2)_5$— group substituted by 4 methyl groups.

6. Process according to claim 1, wherein the organozinc base is a compound of formula (V)

$$(TMP)_x ZnCl_{2-x} \qquad (V)$$

in which x is the number 1 or 2.

7. Process according to claim 1, wherein the organozinc base is present in conjunction with an alkali metal halide or alkaline earth metal halide.

8. Process according to claim 1, wherein the organozinc base is used in a total amount of 0.5 to 5 equivalents, based on the compound Q-H.

9. Process according to claim 1, wherein the compound of formula (I) is used in a total amount of 0.5 to 10.0 equivalents, based on the compound Q-H.

10. Process according to claim 1, wherein the catalyst is a palladium compound.

11. Process according to claim 1, wherein the catalyst is tetrakis(triphenylphosphine)palladium(0).

12. Process according to claim 1, that is conducted in the presence of a solvent selected from the group consisting of tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); N,N'-dimethylpropyleneurea (DMPU); halohydrocarbon, aromatic hydrocarbon, chlorohydrocarbon, tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, 1,2-dichlorobenzene, chlorotoluene, trichlorobenzene; 4-methoxybenzene, fluorinated aliphatic, fluorinated aromatic, trichlorotrifluoroethane, benzotrifluoride and 4-chlorobenzotrifluoride, or a mixture of at least two of these solvents with one another.

13. Process according to claim 12, wherein the solvent is THF or N,N-dimethylformamide (DMF).

14. Process according to claim 1, wherein a) is conducted at a temperature between 0° C. and 80° C.

15. Process according to claim 1, wherein b) is conducted at a temperature between 40° C. and 90° C.

16. Compound of structure Q-H
in which
Q is a structural element from the group of Q1 to Q15

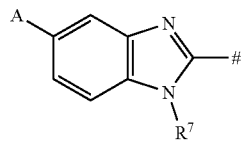 Q1

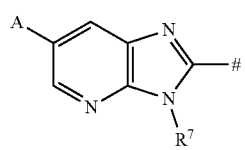 Q2

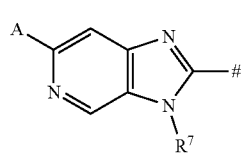 Q3

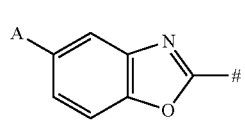 Q4

-continued

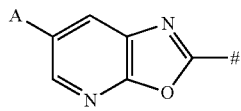 Q5

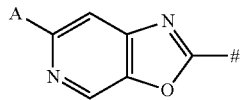 Q6

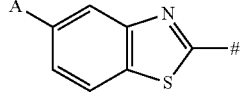 Q7

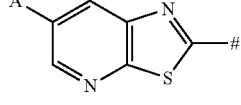 Q8

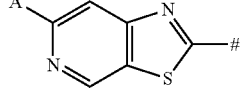 Q9

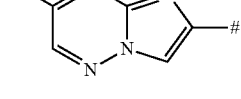 Q10

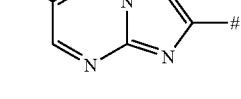 Q11

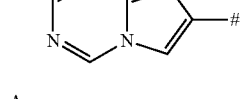 Q12

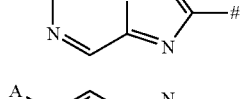 Q13

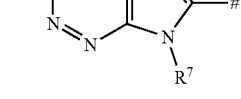 Q14

Q15

$R^7$ is $(C_1-C_4)$alkyl, $(C_1-C_4)$haloalkyl, $(C_1-C_4)$alkoxy-$(C_1-C_4)$alkyl, $(C_1-C_4)$haloalkoxy-$(C_1-C_4)$alkyl, $(C_1-C_4)$alkylthio-$(C_1-C_4)$alkyl, $(C_1-C_4)$alkylsulphinyl-$(C_1-C_4)$alkyl $(C_1-C_4)$alkylsulphonyl-$(C_1-C_4)$alkyl or $(C_1-C_4)$alkylcarbonyl-$(C_1-C_4)$alkyl, A is fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulphinyl or trifluoromethylsulphonyl,

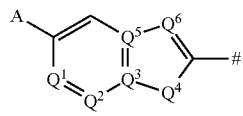

17. Compound of formula (IIIa)

(IIIa)

in which
Q is a structural element from the group of Q1 to Q15

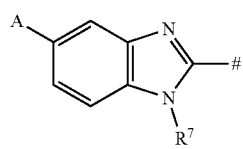

Q1

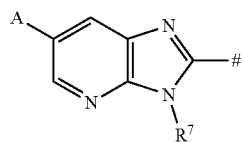

Q2

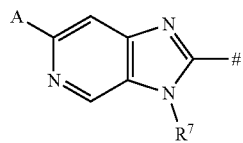

Q3

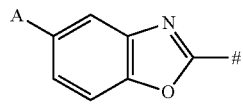

Q4

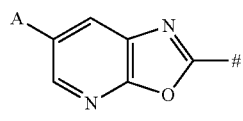

Q5

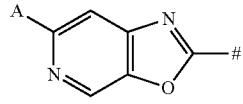

Q6

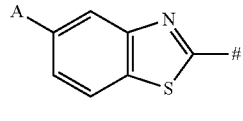

Q7

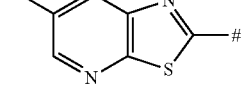

Q8

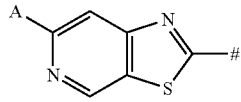

Q9

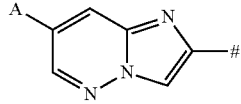

Q10

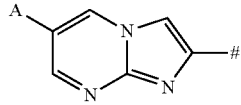

Q11

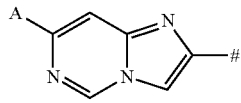

Q12

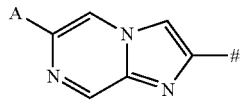

Q13

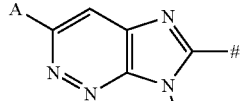

Q14

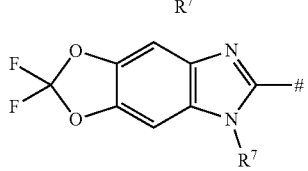

Q15

$R^7$ is $(C_1-C_4)$alkyl, $(C_1-C_4)$haloalkyl, $(C_1-C_4)$alkoxy-$(C_1-C_4)$alkyl, $(C_1-C_4)$haloalkoxy-$(C_1-C_4)$alkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, A is fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulphinyl or trifluoromethylsulphonyl, and $R^2$ is halogen.

18. Compound of formula (IIIb)

Q-Zn-Q  (IIIb)

in which
Q is a structural element from the group of Q1 to Q15

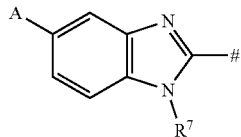

Q1

-continued

Q2 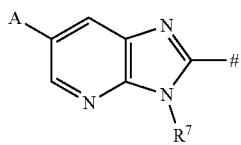

Q3 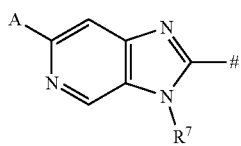

Q4 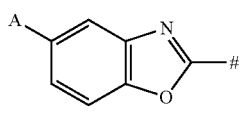

Q5 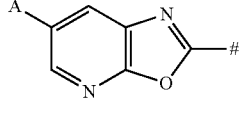

Q6 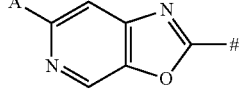

Q7 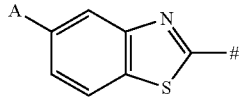

Q8 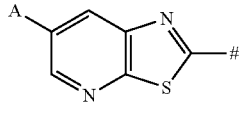

Q9 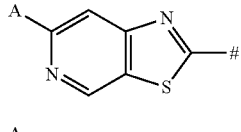

Q10 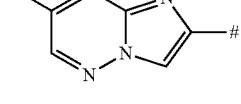

Q11 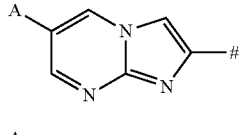

Q12 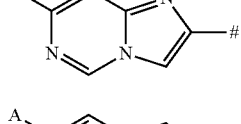

Q13 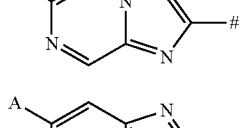

Q14 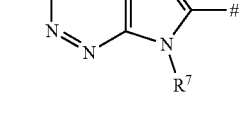

Q15 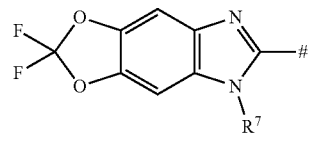

$R^7$ is $(C_1-C_4)$alkyl, $(C_1-C_4)$haloalkyl, $(C_1-C_4)$alkoxy-$(C_1-C_4)$alkyl, $(C_1-C_4)$haloalkoxy-$(C_1-C_4)$alkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, and A is fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulphinyl or trifluoromethylsulphonyl.

19. Compound of formula (II)

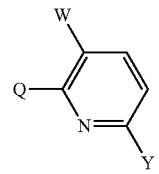

(II)

in which

Q is a structural element from the group of Q1 to Q15

Q1 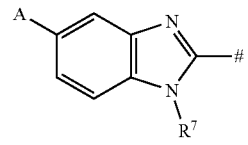

Q2 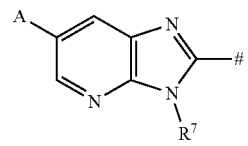

Q3 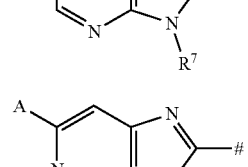

Q4 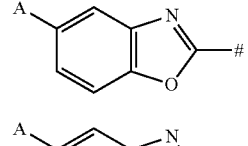

Q5 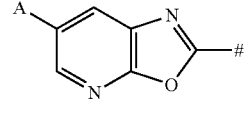

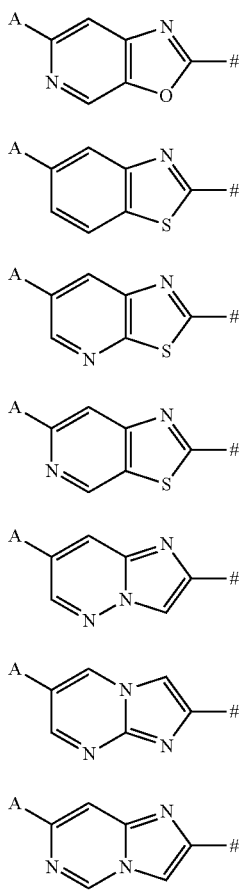

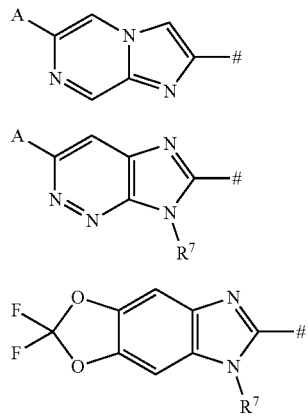

R⁷ is $(C_1-C_4)$alkyl, $(C_1-C_4)$haloalkyl, $(C_1-C_4)$alkoxy-$(C_1-C_4)$alkyl, $(C_1-C_4)$haloalkoxy-$(C_1-C_4)$alkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, A is fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulphinyl or trifluoromethylsulphonyl, W is fluorine or bromine, and Y is fluorine, chlorine, bromine, $CO_2R$ or $NO_2$, where R is $(C_1-C_4)$-alkyl.

* * * * *